US007740835B2

(12) United States Patent
Fujimori et al.

(10) Patent No.: US 7,740,835 B2
(45) Date of Patent: Jun. 22, 2010

(54) ANAEROBIC BACTERIUM AS A DRUG FOR CANCER GENE THERAPY

(75) Inventors: Minoru Fujimori, Matsumoto (JP);
Shun'ichiro Taniguchi, Matsumoto (JP); Jun Amano, Matsumoto (JP);
Kazuyuki Yazawa, Matsumoto (JP);
Yasunobu Kano, Kyoto (JP); Toshiyuki Nakamura, Matsumoto (JP); Takayuki Sasaki, Matsumoto (JP)

(73) Assignee: Anaeropharma Science Inc., Tokyo (JP)

( * ) Notice: Subject to any disclaimer, the term of this patent is extended or adjusted under 35 U.S.C. 154(b) by 0 days.

(21) Appl. No.: 10/782,899

(22) Filed: Feb. 23, 2004

(65) Prior Publication Data
US 2005/0025745 A1     Feb. 3, 2005

Related U.S. Application Data

(63) Continuation of application No. 09/816,391, filed on Mar. 26, 2001, now abandoned.

(30) Foreign Application Priority Data
Sep. 21, 2000   (JP) ............................. 2000-287688

(51) Int. Cl.
A61K 48/00 (2006.01)
C12P 21/04 (2006.01)
C12N 15/85 (2006.01)
(52) U.S. Cl. .................... 424/93.2; 435/252.3; 435/455
(58) Field of Classification Search ................ 435/471; 424/93.4, 93.21
See application file for complete search history.

(56) References Cited

U.S. PATENT DOCUMENTS

| 4,486,407 | A | 12/1984 | Taguchi |
| 6,080,849 | A | 6/2000 | Bermudes et al. |
| 6,190,657 | B1 | 2/2001 | Pawelek et al. |
| 6,416,754 | B1 | 7/2002 | Brown et al. |
| 6,447,784 | B1 | 9/2002 | Bermudes et al. |
| 6,475,482 | B1 | 11/2002 | Escobedo et al. |
| 6,518,062 | B1 * | 2/2003 | Blanche et al. .......... 435/320.1 |
| 6,685,935 | B1 | 2/2004 | Pawelek et al. |
| 6,863,894 | B2 | 3/2005 | Bermudes et al. |
| 6,923,972 | B2 | 8/2005 | Bermudes et al. |
| 6,962,696 | B1 | 11/2005 | Bermudes et al. |
| 7,354,592 | B2 | 4/2008 | Bermudes et al. |
| 2002/0006432 | A1 | 1/2002 | Collins et al. |
| 2002/0182229 | A1 | 12/2002 | Brown et al. |
| 2003/0103952 | A1 * | 6/2003 | Brown et al. ............. 424/93.41 |
| 2004/0219169 | A1 | 11/2004 | Bermudes et al. |
| 2004/0229338 | A1 | 11/2004 | King et al. |
| 2005/0249706 | A1 | 11/2005 | Bermudes et al. |
| 2007/0009489 | A1 | 1/2007 | Bermudes et al. |

FOREIGN PATENT DOCUMENTS

JP          98111517        9/1998
WO          WO 96/11277     10/1995

OTHER PUBLICATIONS

Yazawa et al. Proceedings of the American Association for Cancer Research Annual Meeting, vol. 40, pp. 88, 1999.*
Yazawa et al. (Breast Cancer Research and Treatment, vol. 66, pp. 165-170, 2001).*
Natori et al. vol. 70, Issue 12, Dec. 1988, pp. 1765-1774.*
Goshima et al. (Biochimie, 1990. vol. 72: 207-214).*
Claret et al. (J. Mol. Biol. 1997; 273: 93-104).*
M J Lemmon et al., "Anaerobic bacteria as a gene delivery system that is controlled by the tumor microenvironment", Gene Therapy, vol. 4, 1997, pp. 791-796.
N. Minton et al., "Chemotherapeutic tumor targeting using clostridial spores", FEMS Microbiology Reviews, vol. 17, 1995, pp. 357-364.
Proceedings, Fifty-Ninth Annual Meeting of the Japanese Cancer Association, Oct. 4-6, 2000, Yokohama, Vo. 91 Supplement, No. 1880 as well as its English translation and Verification of translation.
Yazawa et al., Cancer Gene Therapy, vol. 17, pp. 269-274 published on Mar. 27, 2000 as well as a copy of the certificate.
K. Low et al., "Lipid a mutant *Salmonella* with suppressed virulence and TNFα induction retain tumor—targeting in vivo", Nature Biotechnology, vol. 17, Jan. 1999, pp. 37-41.
G. Dachs et al., "Targeting gene expression to hypoxic tumor cells", Nature Medicine, vol. 3, No. 5, May 1997, pp. 515-520.
H. Matsumura et al., "Construction of *Escherichia coli-Bifidobacterium longum* shuttle vector transforming B. *longum* 105-A and 108-A", Biosci. Biotech. Biochem., vol. 61, No. 7, 1997, pp. 1211-1212.
A. Argnani et al., "A convenient and reproducible method to genetically transform bacteria of the *genus Bifidobacterium*", Microbiology, vol. 142, 1996, pp. 109-114.
N. Kimura et al., "Selective localization and growth of *Bifidobacterium bifidum* in mouse tumors following intravenous administration", Cancer Research, vol. 40, Jun. 1980, pp. 2061-2068.
M. Fox et al., "Anaerobic bacteria as a delivery system for cancer gene therapy: in vitro activation of 5-fluorocytosine by genetically engineered clostridia", Gene Therapy, vol. 3, 1996, pp. 173-178.
C. Tacket et al., "Comparison of the Safety and Immunogenicity of ΔaroC ΔaroD and Δcya Δcrp *Salmonella* typhi Strains in Adult Volunteers", Infection and Immunity, vol. 60, No. 2, pp. 536-541, Feb. 1992.1.
H. Yasui et al., "Enhancement of Immune Response in Peyer's Patch Cells Cultured with *Bifidobacterium breve*", Journal of Dairy Science, vol. 74, pp. 1187-1195, 1991.

(Continued)

*Primary Examiner*—Scott Long
(74) *Attorney, Agent, or Firm*—Jones Day

(57) ABSTRACT

The present invention provides a bacterium belonging to the genus *Bifidobacterium*, by which DNA coding for a protein having an antitumor activity or DNA coding for a protein having the activity of converting a precursor of an antitumor substance into the antitumor substance is delivered to tumor tissues specifically under anaerobic conditions thereby expressing the protein encoded by the DNA, as well as a pharmaceutical composition comprising said anaerobic bacterium.

24 Claims, 11 Drawing Sheets

OTHER PUBLICATIONS

D. Salzman et al., "Attenuated *Salmonella typhimurium* Containing Interleukin-2 Decreases MC-38 Hepatic Metastases: A Novel Antitumor Agent", Cancer Biotherapy and Radiopharmaceuticals, vol. 11, No. 2, pp. 145-153, 1996.

J. Saavedra et al., "Feeding of *Bifidobacterium bifidum* and *Streptococcus thermophilus* to Infants in Hospital for Prevention of Diarrhoea and Shedding of Rotavirus", The Lancet, vol. 344, pp. 1046-1049, Oct. 15, 1994.

B. Reddy et al., "Inhibitory Effect of *Bifidobacterium longum* on Colon, Mannary, and Liver Carcinogenesis Induced by 2-Amino-3-methylirnidazo[4,5-*f*]quinoline, a Food Mutagen", Cancer Research, vol. 53, pp. 3914-3918, Sep. 1, 1993.

D. Hone et al., "Evaluation in Volunteers of a Canadidate Live Oral Attenuated *Salmonella typhi* Vector Vaccine", Journal of Clinical Investigation, vol. 90, pp. 412-420, 1992.

M. Babincova et al., Life and medical Sciences Online, (2000), 1, pp. 1-4.

IM Verma et al., Nature, "Gene therapy-promises, problems and prospects," Sep. 1997, vol. 389, pp. 239-242.

WF Anderson, Nature, "Human gene therapy", Apr. 1998, vol. 392, pp. 25-30.

K Yazawa et al., Breast Cancer Research and Treatment, "Bifidobacterium longum as a delivery system for gene therapy of chemically induced rat mammary tumors," 2001, 66, pp. 156-170.

Els Kievit et al.: "Superiority of Yeast over Bacterial Cytosine Deaminase for Enzyme/Prodrug Gene Therapy in Colon Cancer Xenografts," (Cancer Research 59 1417-1421, Apr. 1, 1999).

Li X, Fu GF, Fan YR, Liu WH, Liu XJ, Wang JJ, Xu GX Bifidobacterium adolescentis as a delivery system of endostatin for cancer gene therapy: selective inhibitor of angiogenesis and hypoxic tumor growth. Cancer Gene Ther. Feb. 2003;10(2):105-11.

Yi C, Huang Y, Guo ZY, Wang SR. Antitumor effect of cytosine deaminase/5-fluorocytosine suicide gene therapy system mediated by Bifidobacterium infantis on melanoma. Acta Pharmacol Sin. May 2005;26(5):629-34.

Butel et al. "Clostridial pathogenicity in experimental necrotising enterocolitis in gnotobiotic quails and protective role of bifidobacteria" J Med Microbiol 47: 391-399, 1998.

Meer et al. "Human disease associated with Clostrodium perfringens enterotoxin." Rev Environ Contam Toxicol 150: 75-94, 1997.

Klinger et al. "Clostridium difficile infection: risk factors, medical and surgical management." Dig Dis 18: 147-160, 2000.

Elmer et al. "Biotherapeutic agents. A neglected modality for the treatment and prevention of selected intestinal and vaginal infections." JAMA 275: 870-876, 1996.

Drlica et al. Histonelike proteins of bacteria. Microbiol Rev 51: 301-319, 1987.

Goshima et al. Characterization of HU-like protein from Bifidobacterium longum. Biochimie 72, 207-212, 1990.

Sayre et al. Construction and properties of a temperature-sensitive mutation in the gene for the bacteriophage SPOI DNA-binding protein TF1. J Bacteriol 172: 4672-4681,1990.

U.S. Appl. No. 11/718,680, filed Jun. 25, 2007, Kano et al.

U.S. Appl. No. 11/910,880, filed Oct. 5, 2007, Hamaji et al.

King. et al.. "Tumor-targeted Salmonella expressing cytosine deaminase converted 5-fluorocytosine to 5-fluoruracil and inhibited tumor growth in vivo," Abstract from $89^{th}$ Annual Meeting of American Association for Cancer Research. 1998.

Pawelek, et al., "Tumor targeted Salmonella as a novel anticancer vector," Cancer Res. 57:4537-4544, 1997.

Sznol, et al., "Use of preferentially replicating bacteria for the treatment of cancer," J. Clin. Invest. 105:1027-1030, 2000.

Kohno, et al., "Promoters and autogenous control of the *E. coli* hupA and hupB genes," J. Mol. Biol. 213:27-36, 1990.

Kohno, et al., "Autoregulation of transcription of the hupA gene in *E. coli*, evidence for steric hindrance of the functional promoter domains induced by HU," J. Biochem. 115:1113-1118, 1994.

Tanaka et al., "Properties of DNA-Binding of HU Heterotypic and Homotypic Dimers from *Escherichia coli*," 1993, J. Biochem. 113:568-572.

Wada et al., "Construction and Characterization of the Deletion Mutant of hupA and hupB Genes in *Escherichia coli*," 1988, J. Mol. Biol. 204:581-591.

Kano et al., "Requirement of integration host factor (IHF) for growth of *Escherichia coli* deficient in HU protein," 1990, Gene 89:133-137.

Pontiggia et al., "Protein HU binds specifically to kinked DNA," 1993, Molec. Microbiol., 7(3):343-350.

* cited by examiner

— pBR322 derived from *E. coli*
■ plasmid pTB6 (3.6kb) derived from *B. longum*
☐ *Hind* III-*Eco* RI fragment (1.1kb) derived from *Enterococcus*

— pBR322 derived from *E. coli*
■ plasmid pTB6 (3.6kb) derived from *B. longum*
□ *Hind* III-*Eco* RI fragment (1.1kb) derived from *Enterococcus*
▭▶ CD gene derived from *E. coli*
⬚ *Hind* III-treating fragment of the *B. longum* gene
▦ region containing a promoter for the HU gene derived from *B. longum*
≡ region containing a terminator for the HU gene derived from *B. longum*

— pBR322 derived from *E. coli*
■ HU gene from *B. longum*
▢ Amp$^r$ Ampicillin resistance gene in pBR322 derived from *E. coli*
▢ Tet$^r$ Tetracycline resistance gene in pBR322 derived from *E. coli*
▢ *Hind* III-treating fragment of the *B. longum* gene

ANAEROBIC BACTERIUM AS A DRUG FOR CANCER GENE THERAPY This application is a continuation application of U.S. patent application Ser. No. 09/816,391 filed Mar. 26, 2001, now abandoned, which claims priority to Japanese patent application Serial No. 2000-287688 filed Sep. 21, 2000.

BACKGROUND OF THE INVENTION

1. Field of the Invention

The present invention relates to anaerobic bacteria belonging to the genus *Bifidobacterium* useful for gene therapy of solid tumors, a pharmaceutical composition containing the same, a method of delivering a gene and a method of treating solid tumors by use of the same.

2. Description of the Prior Art

Hypoxic regions are characteristic of solid tumors in animal (Int. J. Radiat. Oncol. Biol. Phys., 10: 695-712(1984)) and occur with high frequency in many types of human solid tumors (Fischer-Verlag, stuttgart, 219-232(1994), New York). Tissue oxygen electrode measurements (i.e. a membrane examination device capable of measuring dissolved oxygen) taken in cancer patients have shown a median range of oxygen partial pressure of 10 to 30 mmHg in tumors, with a significant proportion of readings below 2.5 mmHg, whereas those in normal tissues range from 24 to 66 mmHg.

Accordingly, gene therapy in solid tumors that targets gene expression to hypoxic tumor cells is currently being investigated (Nat. Med. 3: 515-520 (1997)). As a result, it is known that certain species of anaerobic bacteria, including the genera *Clostridium* and *Bifidobacterium*, can selectively germinate and grow in the hypoxic regions of solid tumors after intravenous (i.v.) injection (Cancer Res. 40: 2061-2068 (1980) & 15: 473-478 (1955)).

Further, anaerobic bacteria such as *Clostridia* or *Salmonella* have been examined for the availability as gene delivery vectors (Gene Ther. 4: 791-796 (1997) & 3: 173-178 (1996), FEMS Microbiol. Rev. 17:357-364(1995), Cancer Biother Radio. 11: 145-153 (1996), Nat. Biotechnol. 17: 37-41 (1999)).

However, these bacteria have pathogenicity in humans and are thus not always safe gene delivery vectors in gene therapy of solid tumors. Actually, some reports have demonstrated febrile adverse reactions as side effects after injection with *Clostridium butyricum* spores or oral intake of *Salmonella typhi* (Eur. J. Cancer. 3: 37-41 (1967), J. Clin. Invest. 90: 412-420 (1992), Infect. Immun. 60: 536-541 (1992)).

The genera *Bifidobacterium* and *Lactobacillus*, on the other hand, are Gram-positive and are domestic, nonpathogenic bacteria found in the lower small intestine and large intestine of humans and other animals.

In particular, *Bifidobacterium* strains have widely used for preparation of fermented dairy products in many Asiatic and Western countries, and it is now generally accepted that these bacteria are nonpathogenic. In addition, it is known that these bacteria are not only nonpathogenic but also have health-promoting properties for their host. Such useful properties include e.g. an increase of the immune response (J. Dairy Sci. 74:1187-1195(1991)), inhibition of carcinogenesis (Cancer Res. 53: 3914-3918 (1993)) and protection of the host against viral infection (Lancet. 344: 1046-1049 (1994)), etc.

Despite the increasing attention to these bacteria in the fields of food science, medicine and industry, they have rarely been used in gene therapy.

To be able to exploit the potential of these bacteria for cancer gene therapy, detailed knowledge is required about such basic biological phenomena as cellular metabolism, gene expression, protein secretion and genetics. But little is known about genetic properties of the genus *Bifidobacterium*, mainly due to the lack of efficient and reproducible systems for genetic transfer and adequate selectable markers.

In recent years, however, a system for the convenient and reproducible genetic transformation of stains of the genus *Bifidobacterium* was developed (Microbiology, 142: 109-114 (1996); Biosci. Biotechnol. Biocem. 61: 1211-1212 (1997)).

However, the development of regulatory sequences including a promoter for highly expressing an introduced gene was still not satisfactory.

SUMMARY OF THE INVENTION

An object of the present invention is to provide anaerobic bacteria belonging to the genus *Bifidobacterium* which are effective as gene delivery vectors in gene therapy of solid tumors and safe to humans and animals, as well as a pharmaceutical composition comprising the anaerobic bacteria.

Another object of the present invention is to provide a method of delivering a gene in which DNA effective in gene therapy of solid tumors specifically to tumor tissues under aerobic conditions by use of said anaerobic bacteria as gene delivery vectors, as well as a method of treating solid tumors by expressing a protein encoded by said DNA by use of said method.

The present inventors found that the bacteria of the genus *Bifidobacterium* can be used as gene delivery vectors on the basis of the known facts (a) human and animal solid tumors are in a hypoxic region, (b) the bacteria of the genus *Bifidobacterium* are anaerobes so they hardly grow in normal tissues, but will grow in tumor tissues under anaerobic conditions, and (c) the bacteria of the genus *Bifidobacterium* are less pathogenic than those bacteria (e.g. *Clostridia* and *Salmonella*) used conventionally as gene delivery vectors.

Further, the present inventors examined a system of genetically transforming the bacteria belonging to the genus *Bifidobacterium*, and as a result, they found that an introduced gene can be efficiently expressed by using expression vector containing a promoter and a terminator involved in expressing a gene coding for a histone-like DNA-binding protein (abbreviated herein after to HU protein) (Biochimie, 72: 207-212 (1990)) inherently highly expressed in the bacteria belonging to the genus *Bifidobacterium*, particularly in *Bifidobacterium longum*.

To achieve the object described above, the present inventors made further study to complete the present invention.

That is, the present invention relates to:

(1) A method for delivering a gene in a system for delivering DNA specifically to tumor tissues under anaerobic conditions, wherein a bacterium belonging to the genus *Bifidobacterium* is used as a gene delivery vector and then the DNA delivered specifically to tumor tissues under anaerobic conditions is expressed in said tumor tissues;

(2) A method for delivering a gene in a system for delivering DNA specifically to tumor tissues under anaerobic conditions, wherein a bacterium belonging to the genus *Bifidobacterium* and having the DNA coding for a protein which has a higher activity than in its parent strain is used as a gene delivery vector and then the DNA delivered specifically to tumor tissues under anaerobic conditions is expressed in said tumor tissues;

(3) A method for delivering a gene in a system for delivering DNA specifically to tumor tissues under anaerobic conditions, wherein a bacterium belonging to the genus *Bifidobacterium* transformed with a recombinant DNA having said DNA is used as a gene delivery vector and the DNA delivered specifically to tumor tissues under anaerobic conditions is expressed in the tumor tissues;

(4) The method as described above in any one of (1) to (3), wherein the DNA is selected from the group consisting of: (a) DNA coding for a protein having an antitumor activity, and (b) DNA coding for a protein having an activity of converting a precursor of an antitumor substance into the antitumor substance;

(5) The method as described above in (4), wherein the protein having an antitumor activity is interleukin-2;

(6) The method as described above in (4), wherein the precursor of an antitumor substance is selected from the group consisting of 5-fluorocytosine, 5-aziridino-2,4-dinitrobenzamide, ganciclovir, a glucuronic acid-conjugated antitumor substance and a lysine-conjugated antitumor substance;

(7) The method as described above in (4), wherein the protein having the activity of converting a precursor of an antitumor substance into the antitumor substance is a protein selected from the group consisting of cytosine deaminase, nitroreductase, herpes simplex virus type 1 thymidine kinase and β-glucuronidase;

(8) The method as described above in (3), wherein the recombinant DNA is an expression vector;

(9) The method as described above in (8), wherein the expression vector has a promoter and a terminator functioning in a bacterium belonging to the genus *Bifidobacterium*;

(10) The method as described above in (9), wherein the promoter and terminator are those involved in expressing a gene coding for histone-like DNA-binding protein (HU protein) derived from *Bifidobacterium longum*;

(11) The method as described above in (9), wherein the promoter and terminator are DNAs located at the 1- to 192-positions and at the 472- to 600-positions respectively in the nucleotide sequence set forth in SEQ ID NO: 1;

(12) The method as described above in any one of (1) to (11), wherein the bacterium is *Bifidobacterium longum*;

(13) The method as described above in any one of (1) to (4) or (6) to (12), wherein the bacterium is *Bifidobacterium longum* 105-A/pBLES100-S-eCD (FERM BP-7274);

(14) A method for expressing a gene coding for a protein having an antitumor activity in tissue tumors specifically, which comprises use of the bacterium as described above in any one of (1) to (5) or (8) to (12);

(15) A method for expressing a gene coding for a protein having the activity of converting a precursor of an antitumor substance into the antitumor substance in tissue tumors specifically, which comprises use of the bacterium as described above in any one of (1) to (4) or (6) to (12);

(16) A pharmaceutical composition comprising the bacterium as described above in any one of (1) to (13);

(17) The pharmaceutical composition as described above in (16), wherein the pharmaceutical composition comprises a combination of the bacterium as described above in any one of (1) to (4) or (6) to (13) and the precursor of an antitumor substance;

(18) The pharmaceutical composition as described above in (16), wherein the pharmaceutical composition comprises the bacterium as described above in any one of (1) to (4) or (6) to (13) and the precursor of an antitumor substance;

(19) The pharmaceutical composition as described above in any one of (16) to (18), wherein the bacterium is *Bifidobacterium longum*;

(20) The pharmaceutical composition as described above in any one of (16) to (19), wherein bacterium is *Bifidobacterium longum* 105-A/pBLES100-S-eCD (FERM BP-7274);

(21) A bacterium belonging to the genus *Bifidobacterium*, which is used in the method as described above in any one of (1) to (13);

(22) *Bifidobacterium longum* 105-A/pBLES100-S-eCD (FERM BP-7274);

(23) DNA having the nucleotide sequence set forth in SEQ ID NO: 1;

(24) A method of treating a solid tumor, which comprises use of the method as described above in any one of (1) to (15);

(25) A method of treating a solid tumor, which comprises administering the bacterium as described above in any one of (1) to (4) or (6) to (13) in combination with the precursor of an antitumor substance;

(26) An anaerobic bacterium belonging to the genus *Bifidobacterium* capable of expressing a gene coding for a protein having an antitumor activity in only cancer cells under substantially anaerobic conditions;

(27) An anaerobic bacterium belonging to the genus *Bifidobacterium* capable of expressing a gene coding for a protein having the activity of converting a precursor of an antitumor substance with low toxicity to humans and animals into an antitumor substance in only cancer cells under substantially anaerobic conditions.

DETAILED DESCRIPTION OF THE INVENTION

Figure 1:
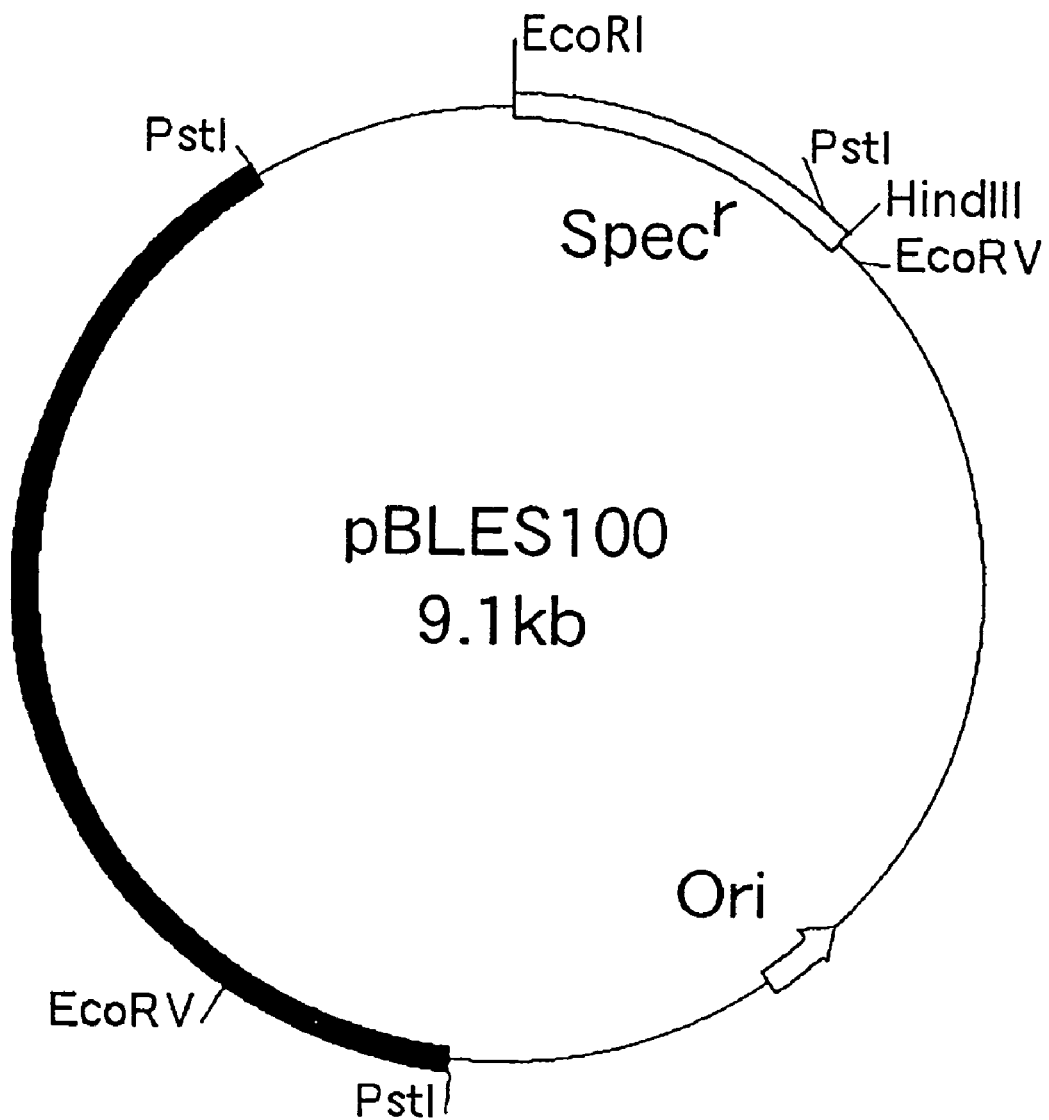
FIG. 1 shows an illustration of plasmid pBLES100. The solid line is *Escherichia coli* vector pBR322, the smeared part is plasmid pTB6 (3.6 kb) derived from *B. longum*, and the non-smeared part is a 1.1-kb Hind III-Eco RI fragment derived from *Enterococcus faecalis*. Spec$^r$ represents a spectinomycin resistance gene, and Ori represents an origin of replication.

The present invention provides bacteria belonging to the genus *Bifidobacterium* (abbreviated hereinafter to the bacteria of the genus *Bifidobacterium*) having a gene coding for a substance having an antitumor activity. Preferably said substance has a higher antitumor activity than in its parent strain.

The substance having a higher antitumor activity than in its parent strain is e.g. the substance which is expressed in a larger amount than in its parent strain, has an improvement in Km value as compared with the counterpart (enzyme) expressed in its parent strain, or is hardly degradable than in the counterpart expressed in its parent strain, resulting in the higher activity. The parent strain in the microbiology usually means the wild stain, from which substains, clones and mutants and the like are derived (Biologic dictionary, third edition, tokyokagakudoujin 1998).

Whether the activity of the substance having an antitumor activity is higher than in its parent strain can be easily determined by a screening method known in the art. For example, the bacteria of the genus *Bifidobacterium* are cultured in a suitable medium, and the produced substance having an antitumor activity is measured for its antitumor activity (expression level, enzyme activity etc.) by a known method.

The substance having an antitumor activity may be any substance having an antitumor activity and its mechanism is not limited. The antitumor activity includes the action of preventing or inhibiting the development, maturation, multiplication or diffusion of tumor cells or tissues, or the activity of regressing tumor cells or tissues. The tumor includes e.g. carcinoma or sarcoma. However, the substance having an antitumor activity in the present invention is usually a polypeptide or a protein whose structure can be encoded by the nucleotide sequence of DNA.

The substance having an antitumor activity in the present invention includes e.g. cytokines. The cytokines having an antitumor activity include e.g. interferon (IFN)-α, β, γ, granulocyte macrophage colony-stimulating factor (GM-CSF), interleukin (IL)-1α, IL-1β, IL-2, IL-3, IL-4, IL-6, IL-7, IL-10, IL-12, IL-13, IL-15, IL-18, anti-Fas antibody, tumor necrosis factor (TNF)-α, lymphotoxin (LT)-β, granulocyte colony-stimulating factor (G-CSF), macrophage colony-stimulating factor (M-CSF), macrophage migration inhibition factor (MIF), leukocyte inhibitory factor (LIF), co-stimulating factor of activated T cell B7 (CD80) and B7-2 (CD86), kit ligand, oncostatin M, etc. In particular, IL-2 is preferable.

These may be a combination thereof. For example, a combination of IL-6 and TNF-α, a combination of IFN-α and IFN-β or IFN-γ, a combination of TNF-α and IFN-γ, and a combination of anti-Fas antibody and IFN-γ are preferable.

The present invention provides those bacteria belonging to the genus *Bifidobacterium* having a gene coding for an enzyme capable of converting a precursor of an antitumor substance with low toxicity to humans and animals into the antitumor substance (referred to hereinafter as converting enzyme), said enzyme being capable of production in only tumor cells under substantially anaerobic conditions. Preferably the converting enzyme has a higher activity than in its parent strain. The converting enzyme having a higher activity than in its parent strain has the almost same meaning as defined above.

The antitumor substance may be any known substance having an antitumor activity. The antitumor activity has the same meaning as defined above. However, the precursor of an antitumor substance should be low toxic to humans and animals. The precursor of an antitumor substance may be in an inactive form. The substance in an inactive form means the one converted by the converting enzyme into an active substance expressing an antitumor activity.

The converting enzyme can be selected as necessary depending on the combination of the precursor of an antitumor substance and the antitumor substance. The converting enzyme may be either a single enzyme or a group of plural enzymes, preferably a single enzyme.

The combination of the precursor of an antitumor substance, the antitumor substance and the converting enzyme used in the present invention is not particularly limited insofar as they are known in the art.

Mention is made of e.g. a combination of 5-fluorocytosine (5-FC) as the precursor of an antitumor substance, 5-fluorouracil as the antitumor substance and cytosine deaminase as the converting enzyme.

Mention is also made of a combination of 5-aziridino-2,4-dinitrobenzamide (CB1954) as the precursor of an antitumor substance, an alkylating agent as the antitumor substance known to form bridge-linkages in double-stranded DNA, and nitroreductase as the converting enzyme.

Mention is also made of a combination of ganciclovir as the precursor of an antitumor substance, its metabolite as the antitumor substance, and herpes simplex virus type 1 thymidine kinase (HSV1-TK) as the converting enzyme.

Further, the antitumor substance may be converted into the precursor rendered low-toxic (e.g. in an inactivated form) to humans by modifying it by conjugation with glucuronic acid, glycine or lysine, and the converting enzyme may be an enzyme for de-modifying said precursor. The enzyme for de-modifying the precursor may be any enzyme known in the art, and for example a combination of a glucuronic acid-conjugated precursor of an antitumor substance and β-glucuronidase as the converting enzyme can be mentioned.

The bacteria of the genus *Bifidobacterium* used in the present invention may be any known strains belonging to the aforementioned genus, which is anaerobic.

Examples thereof include *Bifidobacterium adolescentis, B. longum, B. bifidum, B. pseudolongum, B. thermophirum, B. breve, B. infantis* etc.

Particularly preferably used are those bacteria known to be resident in intestines in humans of any age, such as *B. adolescentis, B. longum, B. bifidum* and *B. infantis*, among which *B. longum* is the most preferable. Further, their resistant strains, mutants etc. may also be used.

Any of these bacteria are commercially available or easily obtainable from the depository organizations. For example,

*Bifidobacterium longum* has been deposited under ATCC-15707, *B. bifidum* under ATCC-11863, and *B. infantis* under ATCC-15697.

The bacteria of the genus *Bifidobacterium* include those strains capable of producing the substance having an antitumor activity or the converting enzyme, and such strains can be used preferably as the gene delivery vectors in the present invention. Such strains include *B. longum* producing cytosine deaminase capable of converting 5-FC into 5-FU.

Whether the bacterium in question is a strain capable of producing the substance having an antitumor activity or the converting enzyme can be easily judged by examining whether the substance having an antitumor activity or the converting enzyme is detected by a known screening method or whether the antitumor substance is detected upon culture of the bacterium in a medium containing a precursor of the antitumor substance.

The strain not capable of producing the substance having an antitumor activity or the converting enzyme is transformed in the following manner with DNA coding for the substance having an antitumor activity or the converting enzyme, whereby the bacterium can be preferably used as the gene delivery vector in the present invention.

The following fundamental procedures in genetic engineering or biological engineering can be conducted according to the methods described commercial books on experiments, such as "Idenshi Manual (Gene Manual)" published by Kodansha, "Idenshi Sosa Jikkenho (Experimental Methods in Gene Manipulation)" edited by Y. Takagi and published by Kodansha, Molecular Cloning, Cold Spring Harbor Laboratory (1982), Molecular Cloning, 2nd ed., Cold Spring Harbor Laboratory (1989), Methods in Enzymology, 194 (1991), "Genetic Experimental Methods by Yeasts", Extra Issue of "Jikken Igaku (Experimental Medicine)" published by Yodosha (1994), etc.

First, it is necessary to obtain DNA coding for the substance having an antitumor activity or the converting enzyme.

The DNA described above can be easily obtained on the basis of the information on the known nucleotide sequence.

For example, it can be obtained by chemical synthesis using a known method on the basis of the information on the known nucleotide sequence. The chemical synthesis method includes e.g. a chemical synthesis method using a DNA synthesizer such as DNA synthesizer model 392 (Perkin Elmer) utilizing the phosphoamidite method.

Alternatively, the DNA described above can also be obtained by amplification of the DNA in the PCR method (PCR Protocols, Academic Press (1990)) where nucleotides prepared on the basis of the 5'- and 3'-terminal nucleotide sequences of said nucleotide sequence are used as the primers, while cDNA synthesized from mRNA contained in tissues or cells in various organisms or cDNA selected from cDNA library is used as the template.

Further, the above-described DNA can also be obtained by colony hybridization or plaque hybridization with cDNA library or cDNA synthesized from mRNA contained in tissues or cells in various organisms (Molecular Cloning, 2nd ed.) where full-length or partial DNA or polynucleotide chemically synthesized on the basis of the information on the known nucleotide sequence is used as the probe.

Alternatively, the above DNA can also be easily obtained from the information on the known amino acid sequence.

As the method of obtaining the above-described DNA from the information on the known amino acid sequence, a method known in the art may be used. Specifically, there is a method of amplifying the desired DNA from the cDNA library etc. by the PCR method using synthetic DNA primers having a partial nucleotide sequence of the DNA coding for the known amino acid sequence, or a selection method by hybridizing the DNA integrated in a suitable vector with a labeled DNA fragment or synthetic DNA (probe) coding for a part or the whole of the substance having an antitumor activity or the converting enzyme.

If the substance or the enzyme is known to have an antitumor activity or a converting enzyme activity, but neither the amino acid sequence thereof nor the nucleotide sequence of DNA coding therefor is known, the method of obtaining the DNA coding for the substance having an antitumor activity or the converting enzyme involves e.g. preparing an expression cDNA library from organisms confirmed to have the antitumor activity or the converting enzyme activity and then screening individual cells constituting the library by using the antitumor activity or converting enzyme activity as the indicator in order to obtain those cells carrying the DNA coding for the substance having an antitumor activity or the converting enzyme.

Further, the substance having an antitumor activity or the converting enzyme can be purified by a combination of methods known in the art, then the N-terminal amino acid sequence of the substance having an antitumor activity or the converting enzyme is analyzed by a method known in the art, and hybridization with the cDNA library etc. is conducted where a synthetic DNA having the nucleotide sequence of DNA coding for said amino acid sequence is used as the probe, whereby the substance having an antitumor activity or the converting enzyme can be obtained.

Specifically, DNA coding for cytosine deaminase is preferably the one isolated from plasmid pAdex1CSCD (RDB No. 1591, Gene Bank, Institute of Physical and Chemical Research) containing DNA coding for cytosine deaminase derived from *E. coli*, or from plasmid pMK116 containing DNA coding for cytosine deaminase derived from *E. coli* (D. A. Mead et al., Protein Engineering 1: 67-74 (1986)).

Nitroreductase is preferably the one isolated from *E. coli* B. Its amino acid sequence is described in Biochem. Pharmacol, 44: 2289-2295, and on the basis of its amino acid sequence, the DNA coding for nitroreductase can be easily obtained by the method described above.

In addition to the DNA coding for the substance having an antitumor activity or the converting enzyme, which is obtained on the basis of the information on the known nucleotide or amino acid sequence, DNA hybridizing with said DNA under stringent conditions can also be used in the present invention. That is, a plurality of genetic codes are generally present for one amino acid, so that even DNA having a nucleotide sequence different from the nucleotide sequence based on the known nucleotide or amino acid sequence or DNA coding for an amino acid sequence different from the known amino acid sequence due to one or several amino acid residues are deleted, substituted or added in the known amino acid sequence can be used in the present invention insofar as it can express the substance having an antitumor activity or the converting enzyme.

The DNA capable of hybridization under stringent conditions means DNA obtained by colony hybridization, plaque hybridization or Southern hybridization with the above-described DNA as the probe.

Specifically, the DNA includes those DNAs which can be identified by hybridization conducted in the presence of about 0.7 to 1.0 M sodium chloride at about 65° C. on a filter onto which DNA derived from colonies or plaques has been immobilized, and then washing the filter under the condition of about 65° C. with about 0.1- to 2-fold conc. SSC solution (1-fold conc. SSC solution consists of 150 mM sodium chloride and 15 mM sodium citrate). Hybridization can be conducted by a method described in e.g. Molecular Cloning, Second Edition, Current Protocols in Molecular Biology, DNA Cloning 1: Core Techniques, A Practical Approach, Second Edition, Oxford University (1995), etc.

Specifically, the hybridizable DNA includes those DNAs having at least 60% or more, preferably about 80% or more and most preferably about 95% or more homology to the nucleotide sequence of DNA coding for the substance having an antitumor activity or the converting enzyme obtained on the basis of the information on the nucleotide sequence or the information on the amino acid sequence described above.

The homology of a nucleotide sequence or an amino acid sequence can be determined using the algorithm "BLAST" by Karlin and Altschl (Proc. Natl. Acad. Sci. USA, 90, 5873-5877 (1993)). The programs called "BLASTN" and "BLASTX" have developed based on the above algorithm (J. Mol. Biol., 215, 403-410 (1990)). In the case of analyzing a nucleotide sequence based on BLAST, the parameter can be set to e.g. score=100, wordlength=12. And in the case of analyzing an amino acid sequence based on BLASTX, the parameter can be set to e.g. score=50, wordlength=3. In the case of using BLAST or Gapped BLAST program, a default parameter of each program can be used. The specific analysis method of using the above programs are known in the art.

In the present invention, it is also possible to employ a protein or a polypeptide having an amino acid sequence wherein one or several amino acid residues are deleted, substituted or added in the amino acid sequence coding for the above substance or converting enzyme.

Such protein or polypeptide can be obtained by site-specific mutation of the DNA coding for the substance having an antitumor activity or the converting enzyme by means of site-specific mutagenesis described in Molecular Cloning, A Laboratory Manual, Second Edition, Cold Spring Harbor Laboratory Press (1989), Current Protocols in Molecular Biology, John Wiley & Sons (1987-1997), Nucleic Acids Research, 10, 6487 (1982), Proc. Natl. Acad. Sci., USA, 79, 6409 (1982), Gene, 34, 315 (1985), Nucleic Acids Research, 13, 4431 (1985), Proc. Natl. Acad. Sci. USA, 82, 488 (1985) etc.

The number of amino acids deleted, substituted or added is not particularly limited, but preferably one to dozens, particularly one to few amino acids are deleted, substituted or added.

Secondly, a recombinant DNA containing the DNA coding for the substance having an antitumor activity or the converting enzyme obtained as described above is prepared. In the present invention, the recombinant DNA is preferably an expression vector.

The expression vector can be produced for example by cutting out the desired DNA fragment and ligating the DNA fragment to a region downstream from a promoter in a suitable expression vector.

As the DNA fragment inserted into the expression vector, the DNA coding for the substance having an antitumor activity or the converting enzyme can be used as such or after digestion with restriction enzymes if necessary or after addition of a linker. The DNA fragment may have ATG as the translation initiation codon at the 5'-terminal or TAA, TGA or TAG as the translation termination codon at the 3'-terminal. These translation initiation and termination codons can also be added via a suitable synthetic DNA adaptor to the DNA coding for the substance having an antitumor activity or the converting enzyme.

For expression or advantageous expression of the substance having an antitumor activity or the converting enzyme according to the present invention, the expression vector usually has regulatory sequences added to a cloning vector as described below. Each regulatory sequence may be endogenous or extraneous to the cloning vector.

Such regulatory sequences include, but are not limited to, a promoter, a leader, a pro-peptide sequence, an enhancer, a signal sequence, a selective marker and a terminator. In particular, the regulatory sequences are preferably those containing at least a promoter and a terminator.

The regulatory sequences may have a linker (restriction enzyme cleavage site) to facilitate linkage thereof to the DNA coding for the substance having an antitumor activity or for the converting enzyme or to facilitate linkage between the regulatory sequences described above.

The promoter and terminator used in the present invention are particularly preferably those involved in expression of HU gene (DNA sequence is disclosed as SEQ ID NO: 1, Amino acid sequence is disclosed as SEQ ID NO: 4) that is expressed inherently highly in B. longum. Specifically, it is preferable that the DNA containing the DNA located in the 1- to 192-positions in SEQ ID NO: 1 is used as the promoter and the DNA in the 472- to 600-positions in SEQ ID NO: 1 as the terminator.

The expression vector having the promoter and terminator involved in expressing the HU gene is constructed preferably by cutting the HU gene out from DNA of B. longum with a restriction enzyme, integrating it in a cloning vector described below, and integrating e.g. the DNA coding for the substance having an antitumor activity or for the converting enzyme in a region downstream from the promoter involved in expression of the HU gene. By use of the promoter and terminator involved in expression of the HU gene, the substance having an antitumor activity or the converting enzyme can be efficiently expressed.

The method of isolating the HU gene involves e.g. digesting the chromosomal DNA of B. longum with a restriction enzyme Hind III.

Specifically, the following method can be mentioned. The chromosomal DNA of B. longum is digested with a restriction enzyme Hind III and purified by phenol treatment and ethanol precipitation. Separately, pBR322 (Takara Shuzo Co., Ltd.) is also digested with Hind III, dephosphorylated, and purified in analogous manner. The respective DNAs are ligated to give a recombinant DNA.

This recombinant DNA is then used to transform E. coli mH3 (Gene, 45, 37 (1986)) in a usual manner, whereby an ampicillin-resistant and tetracycline-sensitive transformant is obtained. A plasmid DNA is extracted in a usual manner from the transformant thus obtained, and the plasmid DNA is introduced in a usual manner into E. coli YK2741 strain (Gene, 89, 133 (1990)) thereby transforming said strain. The YK2741 strain is deficient in HU gene and IHF (integration host factor) gene and is thus sensitive to low temperatures, and the capability of its low-temperature sensitivity can be utilized for selection of the transformant containing the DNA encoding for HU by plating it onto an ampicillin-containing agar medium and culturing it at 27° C.

Then, the YK2741 transformant thus obtained is further cultured, and a plasmid possessed in said strain is extracted in a usual manner, and the plasmid DNA is introduced in a usual manner into E. coli YK1340 strain (J. Mol. Biol., 204, 581 (1988)) thereby transforming said strain. The resulting transformant is subjected in a usual manner to a test of infection with Mu phage. The YK1340 strain is a strain deficient in HU gene, but Mu phage necessitates the HU protein for its growth, and thus a transformant infected with Mu phage and lyzed by growth of Mu phage therein is a promising candidate for a strain carrying the HU gene derived from B. longum.

Accordingly, plasmid pBLHU15 having the promoter and terminator involved in expression of the HU gene derived from *B. longum* can be obtained by selecting the plasmid possessed in the strain resistant to ampicillin and infected with Mu phage and lyzed by growth of Mu phage therein.

By further integrating a signal sequence therein, the substance having an antitumor activity or the converting enzyme produced e.g. in host cells can be positively secreted into the outside of the host cells. That is, the signal sequence can be used to express the substance having an antitumor activity or the converting enzyme in a form having a signal peptide, resulting in positive secretion of the substance having an antitumor activity or the converting enzyme into the outside of the host cells.

The method of adding the signal peptide includes e.g. the method of Paulson et al. (J. Biol. Chem., 264, 17619 (1989)), the method of Low et al. (Proc. Natl. Acad. Sci., USA, 86, 8227 (1989), Genes Develop., 4, 1288 (1990)), or by the methods described in JP-A 5-336963, WO94/23021, etc.

The selective marker is used for specifically selecting the transformed bacteria of the genus *Bifidobacterium*. For example, mention is made of selection by chemical resistance markers with ampicillin resistance, tetracycline resistance, neomycin resistance or kanamycin resistance; nutrition requirements; and mediums such as HAT medium etc.

If the cloning vector described below has the selective marker, integration of another additional selective marker is not necessary.

The cloning vector that can be used in the present invention includes a cloning vector (a) capable of easily producing a recombinant vector in vitro with the DNA coding for the substance having an antitumor activity or for the converting enzyme, (b) having the ability to autonomously replicate in the bacteria of the genus *Bifidobacterium* or to integrate into genomic DNA of the bacteria of the genus Bifidobacterium, (c) capable of being introduced into the bacteria of the genus *Bifidobacterium*, and (d) permitting specific detection of the bacteria of the genus *Bifidobacterium* transformed by introducing the cloning vector.

As the cloning vector, plasmid pBLES100 is specifically mentioned, and this plasmid can be used preferably in the present invention.

This plasmid is illustrated in FIG. 1. As can be seen from FIG. 1, a 1.1-kb Hind III-EcoRI fragment (the non-smeared part in FIG. 1) derived from *Enterococcus faecalis* is integrated in a composite plasmid consisting of *Escherichia coli* vector pBR322 (the solid line in FIG. 1) and *B. longum*-derived pTB6 plasmid (3.6 kb) (the smeared part in FIG. 1). This fragment contains a region showing spectinomycin resistance, that is, a region coding for spectinomycin adenyltransferase.

Figure 2:
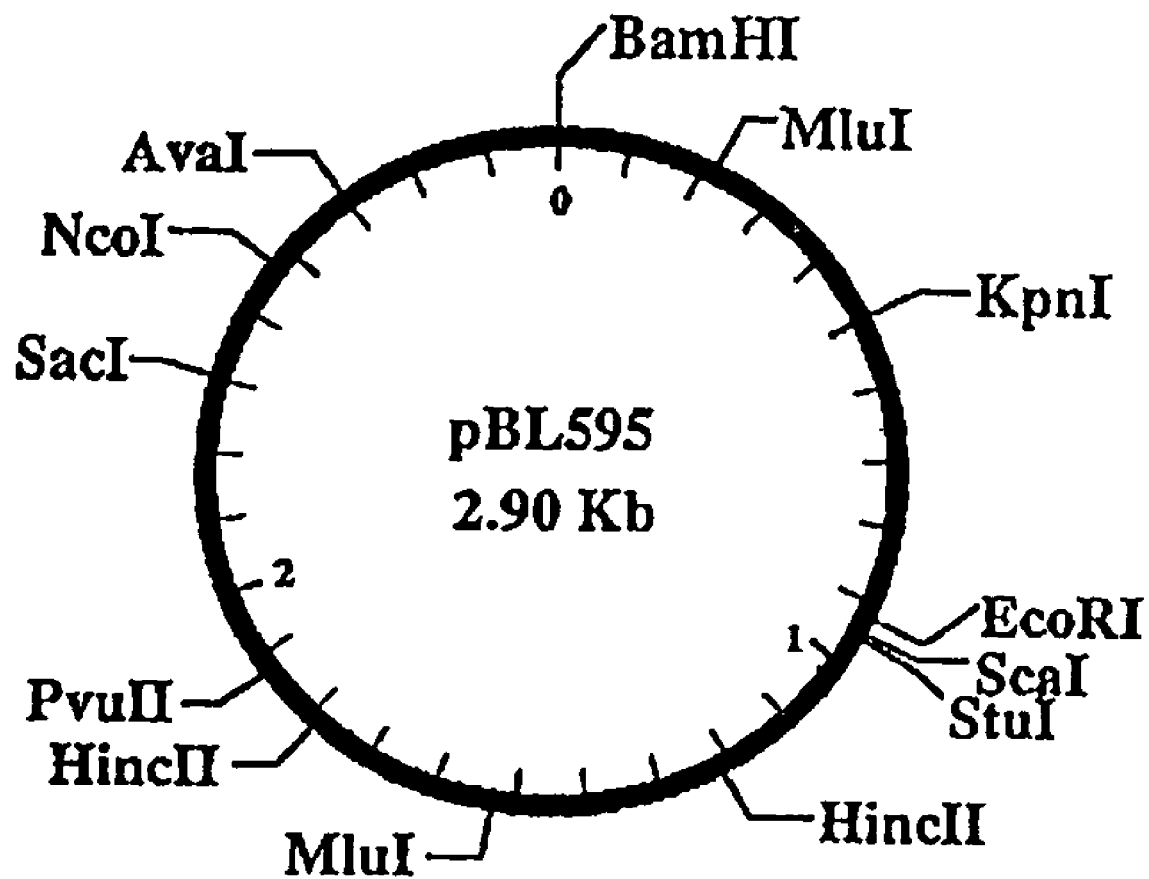
FIG. 2 shows an illustration of plasmid pBL595.

Mention is also made of plasmid pBL595 of about 2.9 kb in size derived from *B. longum* SBT595 (FERM P-14162 deposited with the National Institute of Bioscience and Human-Technology, Agency of Industrial Science and Technology, Japan) and having restriction enzyme recognition sites shown in FIG. 2.

Figure 3:
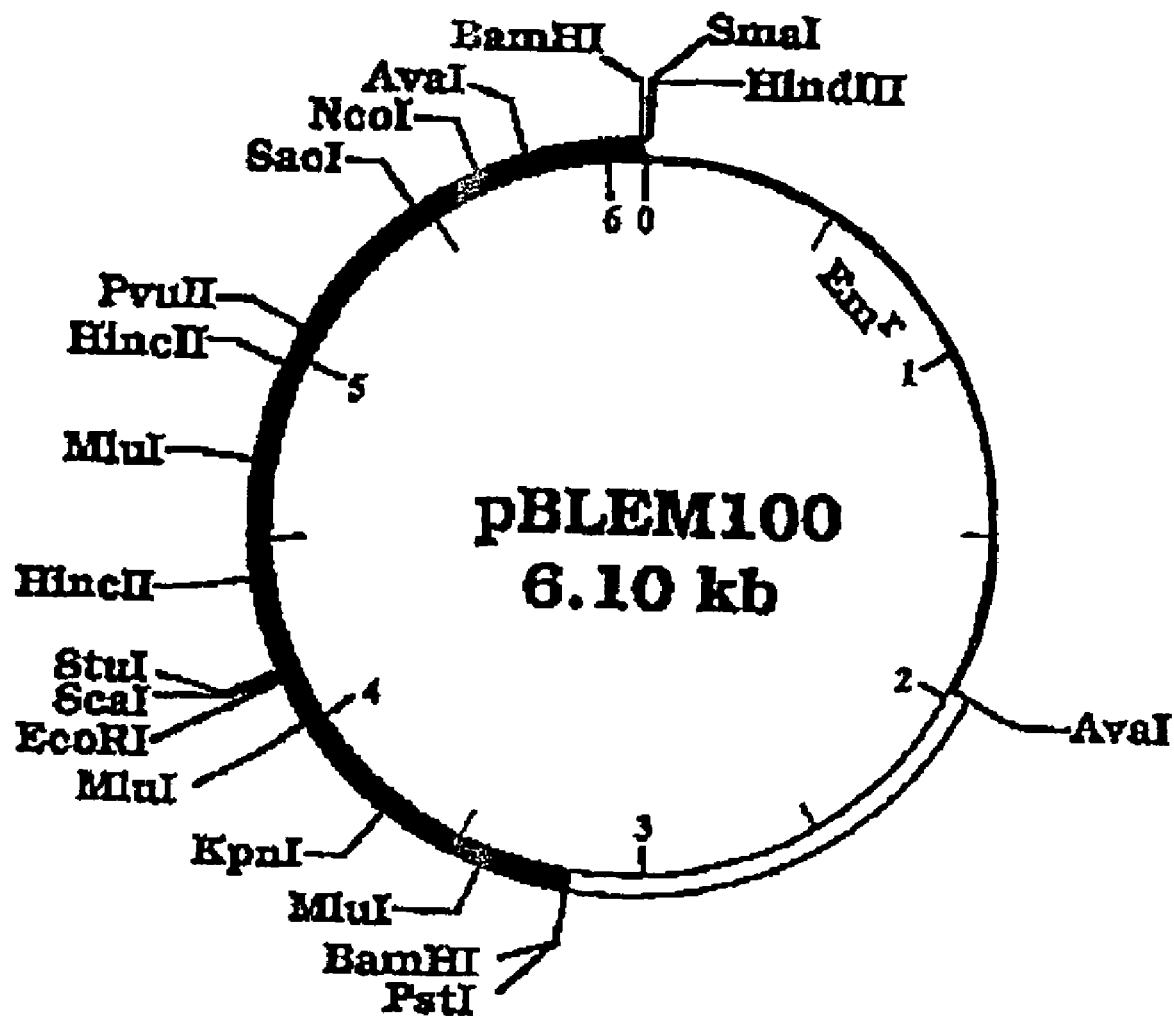
FIG. 3 shows an illustration of plasmid pBLEM100. The smeared part is plasmid pBL595 derived from *B. longum* SBT595, the non-smeared part is an Ava I-Hind III fragment of pBR329 derived from *Escherichia coli*, and the solid line is a Hind III-Ava I fragment of pAMβ1 derived from *Enterococcus faecalis*.

Mention is also be made of plasmid pBLEM100 (FIG. 3) consisting of plasmid pBL595, an Ava I-Hind III fragment from *E. coli*-derived pBR329, and a Hind III-Ava I fragment from pAMβ1 derived from *Enterococcus faecalis*. *E. coli* carrying the plasmid pBLEM100 has been deposited under FERM P-14102 with the National Institute of Bioscience and Human-Technology, Agency of Industrial Science and Technology, Japan.

Further, a plasmid vector constructed by binding a conjugated plasmid consisting of a plasmid derived from a bacterium belonging to the genus *Streptococcus* and a plasmid from *E. coli* to plasmid pBL67 or pBL78 derived from *B. longum* may also be used (JP-A 5-130876).

Figure 4:
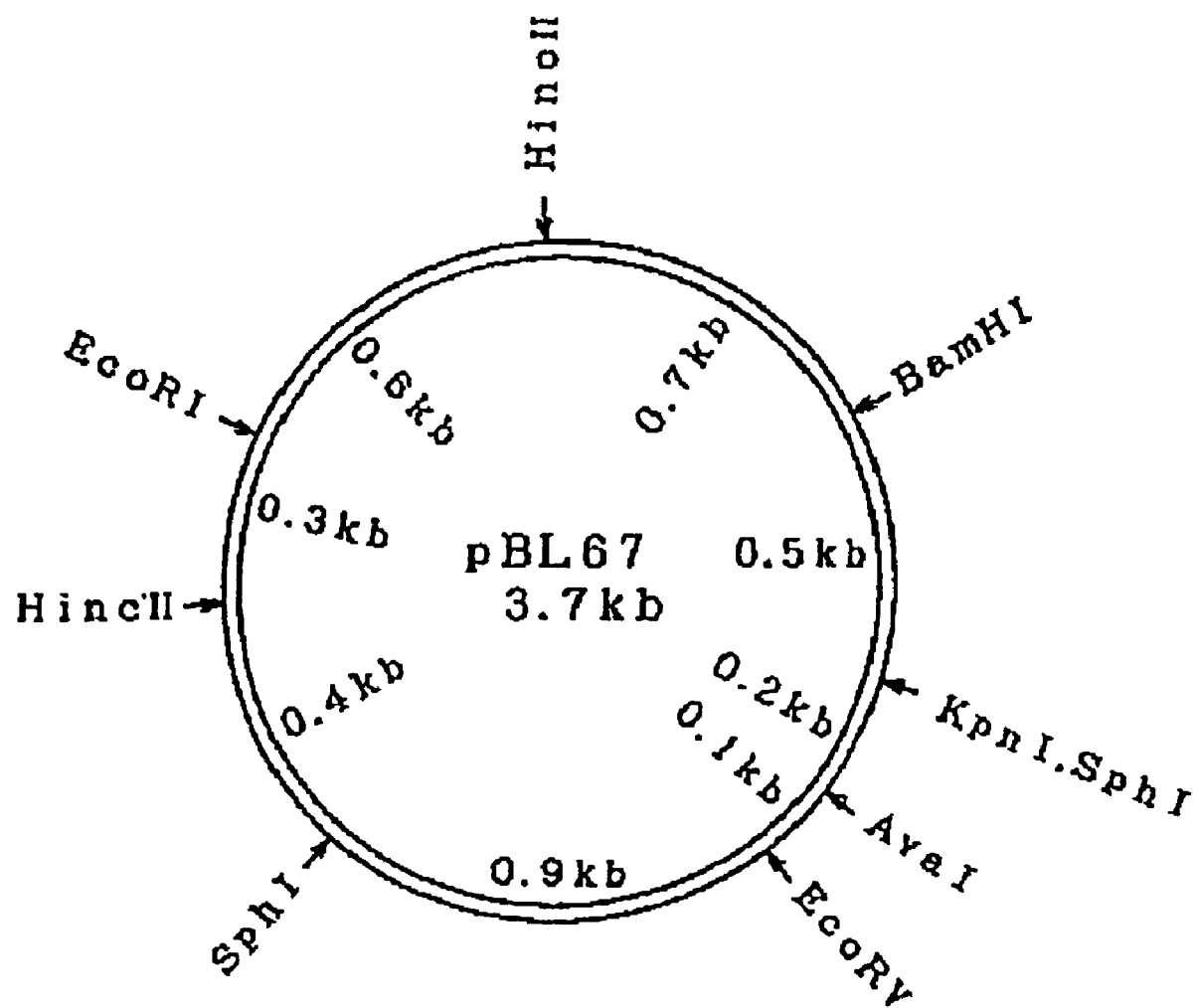
FIG. 4 shows an illustration of plasmid pBL67.
Figure 5:
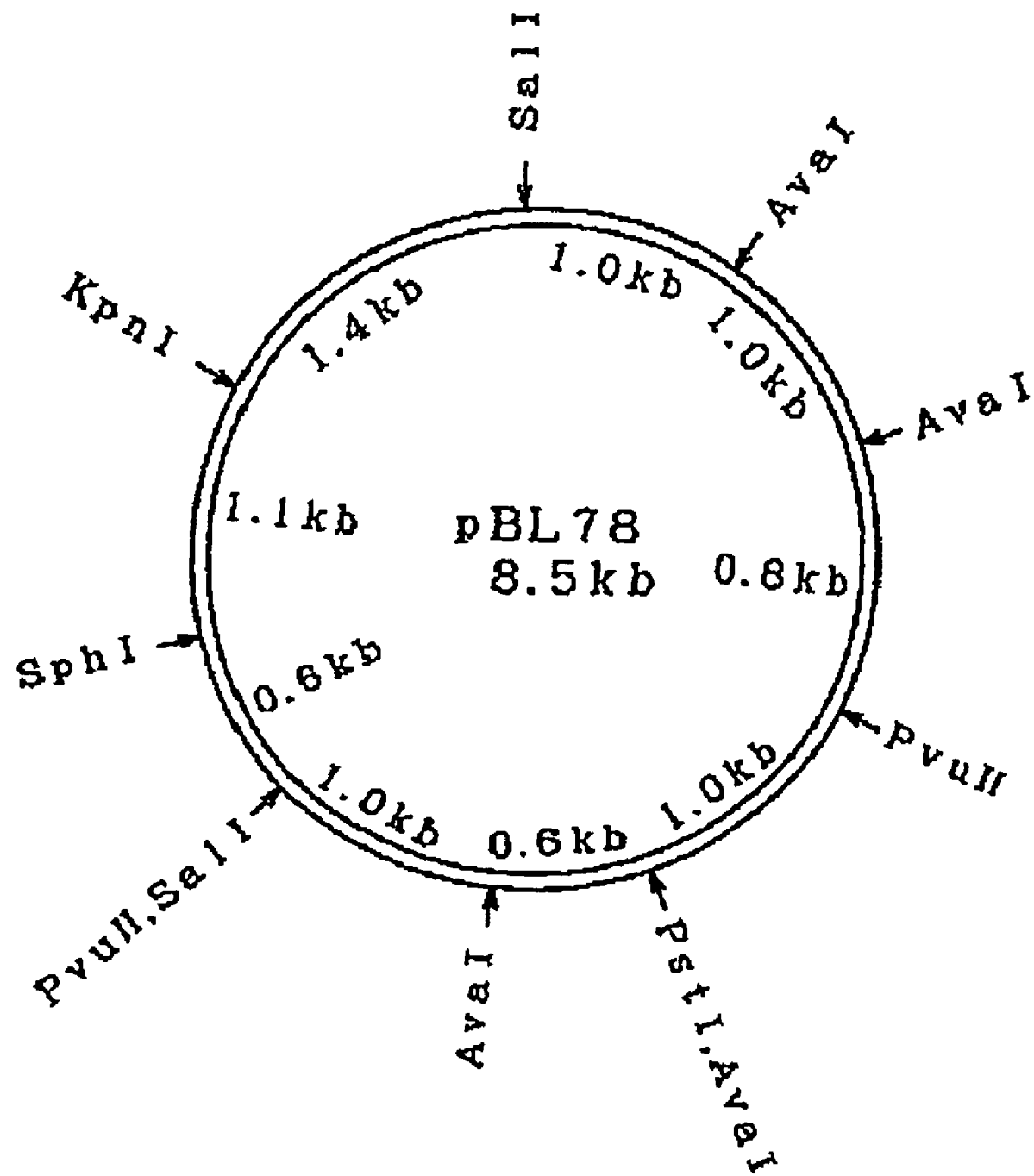
FIG. 5 shows an illustration of plasmid pBL78.

Plasmid pBL67 is an about 3.7-kb plasmid having restriction enzyme recognition sites shown in FIG. 4, which was derived from *B. longum* MO9101 (FERM P-12167) or *B. longum* MO9102 (FERM P-12168). Plasmid pBL78 is an about 8.5-kb plasmid having restriction enzyme recognition sites shown in FIG. 5, which was derived from *B. longum* MO9103 (FERM P-12169).

A plasmid in which plasmid pBR322 derived from *E. coli* is bound to plasmid pTB4, pTB6 or pTB10 derived from *B. longum* is also mentioned. Further, a plasmid in which the whole of pC194 (or a chloramphenicol resistance gene therein) derived from *Staphylococcus oureus* is bound to the above plasmid is also mentioned. Further, a plasmid in which genes involved in tryptophan synthetic pathway from *B. longum* is bound to each of the above two plasmids may also be used (JP-A 63-123384).

Those *E. coli* bacteria carrying these plasmids have been deposited with the National Institute of Bioscience and Human-Technology, Agency of Industrial Science and Technology, Japan (FERM P-9040, 9041, 9042, 9043, 9044, 9045, 9046, 9047 and 9048).

Plasmid pTB4 or pTB10 is a plasmid derived from *B. longum* BK25 (FERM P-9049). Plasmid pTB6 is a plasmid derived from *B. longum* BK51 (FERM P-9050).

As a preferable embodiment of the expression vector in the present invention, there is an expression vector wherein the promoter and terminator involved in expression of the HU gene described above, and a gene (CD gene) coding for cytosine deaminase (abbreviated hereinafter to CD) capable of converting 5-FC into 5-FU, have been integrated in the vector pBLES100 described above.

Figure 6:
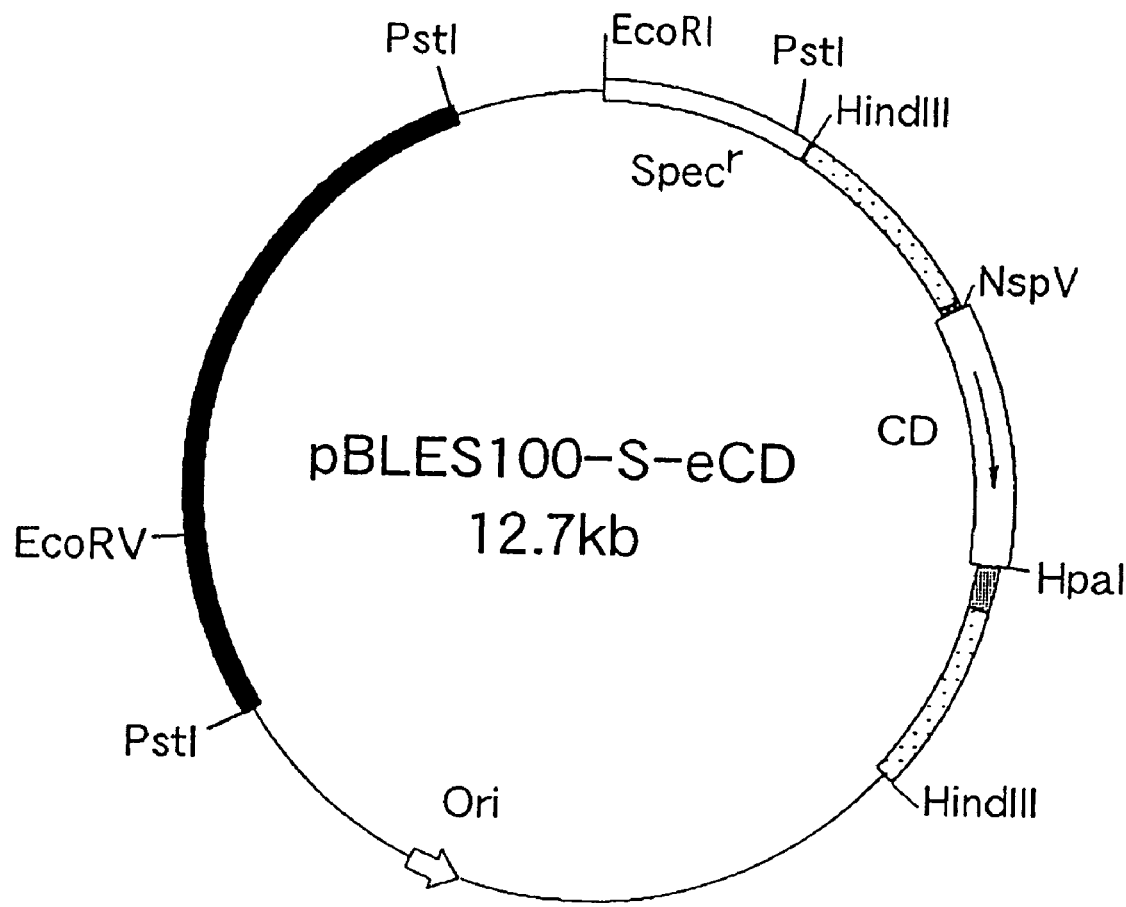
FIG. 6 shows an illustration of plasmid pBLES100 having a HU gene and a cytosine deaminase (abbreviated hereinafter to CD) gene integrated into it. The solid line is *Escherichia coli* vector pBR322, the smeared part is plasmid pTB6 (3.6 kb) derived from *B. longum*, the non-smeared part is a 1.1-kb Hind III-Eco RI fragment derived from *Enterococcus faecalis*, the dotted part is a Hind III-treated fragment from a gene in *B. longum*, the non-smeared part with the arrow inside is a CD gene derived from *Escherichia coli*, the netted part located upstream (toward Ori) from the CD gene is a region containing a promoter for the HU gene, and the shaded part located downstream from the CD gene is a region containing a terminator. Spec$^r$ represents a spectinomycin resistance gene, and Ori represents an origin of replication.

As a more specific embodiment, there is an expression vector illustrated in FIG. 6. By way of example, a method of constructing this expression vector is as follows: A recombinant DNA comprising the *E. coli*-derived CD gene inserted into TOPO vector (Funakoshi Co., Ltd.) is used to transform *E. coli* JM109, and plasmid DNA is extracted from the resulting transformant. The desired plasmid pTOPO-eCD is digested with restriction enzymes Nsp V and Hpa I, followed by purification of the desired 1.3-kb CD-coding DNA fragment.

Similarly, plasmid pBLHU15 carrying the promoter and terminator involved in expression of the *B. longum*-derived HU gene obtained in the manner described above is also digested with Nsp V and Hpa I, followed by purification of the desired 6.7-kb DNA fragment.

The 1.3-kb and 6.7-kb DNA fragments obtained above are ligated in a usual manner to prepare a recombinant DNA, and this recombinant DNA is used to transform *E. coli* JM109 in a usual manner.

Then, the plasmid DNA is extracted in a usual manner from the resulting transformant, then the plasmid DNA is digested with Hind III, and the promoter and terminator involved in expression of the HU gene and a 3.6-kb DNA fragment containing the CD gene are separated and purified by conventional techniques such as agarose gel electrophoresis. Separately, the *Escherichia-Bifidobacterium* shuttle vector pBLES100 described above is also digested with Hind III and dephosphorylated.

The 3.6-kb DNA fragment and the above Hind III digest of pBLES100 are ligated in a usual manner to construct a recombinant DNA, and this recombinant DNA is used to transform *E. coli* JM109 in a usual manner. The transformant can be selected by spectinomycin resistance. The *Escherichia*-Bifidobacterium shuttle vector pBLES100-S-eCD having the CD-coding gene downstream from the promoter for the HU gene can thus be constructed.

Thirdly, the recombinant DNA, preferably an expression vector thereof, is introduced into the bacteria of the genus *Bifidobacterium* as the host. For this introduction, any methods known in the art can be used. Such methods include e.g. the electroporation method (Cytotechnology, 3, 133 (1990)), the calcium phosphate method (JP-A 2-227075), the lipofection method (Proc. Natl. Acad. Sci., USA, 84, 7413 (1987)), the method of using calcium ion (Proc. Natl. Acad. Sci. USA, 69, 2110 (1972)), the protoplast method (JP-A 63-2483942), and those methods described in Gene, 17, 107 (1982), Molecular & General Genetics, 168, 111 (1979), etc.

In the present invention, the electroporation method is preferably used. Electroporation is carried out for about 4.1 to 4.5 ms under the conditions of about 10.0 kV/cm, about 200Ω and about 25 μF.

Although a combination of the recombinant DNA (preferably its expression vector) introduced and the bacterium of the genus *Bifidobacterium* as the host is not particularly limited, plasmid pBLES100 is introduced preferably into *B. longum* 105-A or 108-A (Biosci. Biotech. Biochem. 61(7), 1211-1212 (1997)).

*B. longum* 105-A/pBLES100-S-eCD i.e. *B. longum* 105-A transformed with plasmid pBLES100-S-eCD in which the promoter and terminator involved in expression of the HU gene shown in FIG. 6 and the CD gene were integrated has been deposited under FERM BP-7274 with the National Institute of Bioscience and Human-Technology, Agency of Industrial Science and Technology.

The bacteria of the genus *Bifidobacterium* into which the above expression vector was introduced are cultured in a known medium in which only the transformed bacteria are selected. As the medium, a known medium suitable for the intended strain can be selected as necessary. Depending on the selective marker used, a chemical, an amino acid or the like has been added to the medium to select the transformed bacteria of the genus *Bifidobacterium*.

For example, *B. longum* BK25 or BK51 strain is cultured preferably in a Briggs medium having the following composition:

| Briggs medium | |
| --- | --- |
| Tomato juice extract (*1) | 400 ml |
| Glucose | 20 g |
| Soluble starch | 0.5 g |
| Yeast extract | 6 g |
| Peptone | 15 g |
| Monosodium glutamate | 2 g |
| Tween 80 | 1 g |
| Sodium acetate · 3H$_2$O | 10 g |
| Potassium dihydrogen phosphate | 4 g |
| Sodium chloride | 5 g |
| Distilled water | 600 ml |
| pH | 6.8 |

(*1) A product obtained by mixing a commerciaal tomato juice with an equal volume of distilled water, keeping it at 60° C. for 1 hour and then at 100° C. for 5 minutes, and removing residues therefrom.

*B. longum* SBT0595 strain is cultured preferably in a TGAM medium having the following composition:

| Composition of the TGAM medium | |
| --- | --- |
| Tomato juice extract | 400 ml |
| Peptone | 10 g |
| Yeast extract | 5 g |
| Liver extract powder | 1.2 g |
| Glucose | 3 g |
| Soluble starch | 5 g |
| Sodium chloride | 3 g |
| Tween 80 | 1 g |
| L-cysteine-HCl · H$_2$O | 0.3 g |
| Soybean peptone | 3 g |
| Proteose peptone | 10 g |
| Digested serum powder | 13.5 g |
| Meat extract | 2.2 g |

For example, *B. longum* 105-A or 108-A strain is cultured preferably in the Briggs medium having the same composition as described above except that glucose is exchanged with 2% lactose, 0.2 g/L L-cysteine and 3.4 g/L sodium ascorbate are added thereto.

*B. longum* MO9101, MO9102 and MO9103 strains are cultured preferably in GAM bouillon liquid medium (Nissui Seiyaku Co., Ltd.).

The above bacteria belonging to the genus *Bifidobacterium* can be cultured in the following manner. If the bacteria are cultured in the liquid medium described above, a sufficient amount of the bacteria belonging to the genus *Bifidobacterium* are inoculated into the liquid medium, and they are cultured under anaerobic conditions at about 30 to 40° C., preferably about 37° C. for about 12 hours or more, preferably until their growth reaches the middle phase of logarithmic growth. The aerobic conditions are those conditions achieved in a completely airtight vessel (e.g. an anaerobic chamber or an anaerobic box) capable of keeping the anaerobic degree at which the bacteria belonging to the genus *Bifidobacterium* can grow.

The above-described transformed bacteria of the genus *Bifidobacterium* can grow only in tumor tissues under anaerobic conditions, to express the substance having an antitumor activity or the converting enzyme in the tumor tissues. Accordingly, such transformants of the genus *Bifidobacterium* can be used as a pharmaceutical composition effective for treating tumors preferably solid tumors under anaerobic conditions.

The administration route of the pharmaceutical composition of the present invention includes, but is not limited to, oral or parenteral administration, preferably parenteral administration. The parenteral administration includes administration into the respiratory tract or rectum, or subcutaneous, intramuscular or intravenous administration.

Examples of the pharmaceutical composition suitable for oral administration include e.g. tablets, granules, finely divided agents, powders, syrups, solutions, capsules and suspensions, while examples of the pharmaceutical composition suitable for parenteral administration include e.g. injections, drip infusions, inhalations, sprays, suppositories, and agents absorbed through the skin or mucous membrane, etc.

The pharmaceutical composition of the present invention is used preferably as an injection, particularly as an intravenous injection.

The transformed bacteria of the genus *Bifidobacterium* described above may be subjected to post-treatment known in the art.

The transformed bacteria may be purified in a crude form by e.g. centrifugation. Also, the transformed bacteria may be purified in a crude form and then dissolved or suspended in conventionally used solvent such as physiological saline, PBS (phosphate-buffered saline) or a Ringer's solution blended with lactic acid.

If desired, the bacteria may be lyophilized or spray-dried to form powders or particles.

As the pharmaceutical composition of the present invention, the solution, the suspension or the granular or powdery dried product of the transformed bacteria of the genus *Bifidobacterium* may be administered as such. However, it is generally desired to administer a pharmaceutical composition containing the above-described substance as the active ingredient and one or more additives for the pharmaceutical composition.

Such a pharmaceutical composition can be produced in a known method or a conventional method in pharmacology.

For production of the liquid pharmaceutical compositions suitable for oral administration, it is possible to employ water and pharmaceutical additives e.g. sugars such as sucrose, sorbitol, fruit sugar etc.; glycols such as polyethylene glycol, propylene glycol etc.; oils such as sesame oil, olive oil, soybean oil etc.; and preservatives such as p-hydroxybenzoates.

For production of solid pharmaceutical compositions such as capsules, tablets, powders and granules, it is possible to employ e.g. fillers such as lactose, glucose, sucrose and mannitol; disintegrating agents such as starch and sodium alginate; lubricants such as magnesium stearate and talc; binders such as polyvinyl alcohol, hydroxypropyl cellulose and gelatin; surfactants such as fatty esters; and plasticizers such as glycerin.

Among those pharmaceutical compositions suitable for parenteral administration, the compositions for administration into blood vessels, for example injections and drip infusions can be prepared preferably using an aqueous medium isotonic to human blood.

For example, the injections can be prepared in a usual manner as solution, suspension or dispersion by using an aqueous medium selected from a salt solution, a glucose solution and a mixture of a salt solution and a glucose solution, along with suitable auxiliary agents.

The suppositories for administration into intestines can be prepared using carriers such as cacao fat, hydrogenated fats or hydrogenated carboxylic acids.

The sprays can be prepared using carriers which do not irritate the oral cavity or the mucous membrane in the respiratory tract mucus in humans and can disperse the active ingredient of the present invention i.e. the bacteria of the genus *Bifidobacterium* into fine particles thereby promoting absorption thereof. Such carriers include e.g. lactose and glycerin. Depending on the properties of the present bacteria of the genus *Bifidobacterium* and the carriers used, the pharmaceutical composition can be prepared in the form of aerosol or dry powder.

For production of the parenteral pharmaceutical compositions, it is possible to use one or more pharmaceutical additives selected from diluents, perfumes, preservatives, fillers, disintegrating agents, lubricants, binders, surfactants and plasticizers.

The form of the pharmaceutical composition of the present invention as well as the process for producing the same is not limited to those exemplified above.

The dose of the pharmaceutical composition of the present invention and the frequency of administration thereof are not particularly limited and can be selected as necessary depending on various conditions such as the type of the gene possessed by the bacteria of the genus *Bifidobacterium*, the type of the morbid state to be treated, the administration route, the age and body weight of the patient, the symptoms, and the severeness of the disease. For e.g. systemic administration thereof by intravenous injection, about $2 \times 10^6$ to $2 \times 10^7$ bacteria/body are administered daily to an adult, and for topical administration thereof into tumors, about $5 \times 10^8$ bacteria are administered preferably per tumor. However, the dose is not limited to this specific example.

The pharmaceutical composition according to the present invention can be applied to tumors under anaerobic conditions, preferably various solid tumors. The solid tumors include e.g. colon (large intestine) cancer, cerebral tumor, head cervical cancer, breast cancer, lung cancer, esophagus cancer, stomach cancer, hepatic cancer, cholecystic cancer, bile-duct cancer, pancreatic cancer, Langerhans islet cancer, chorionic cancer, colon cancer, renal cell cancer, adrenal cortical cancer, bladder cancer, testicle cancer, prostate cancer, testicle tumor, ovary cancer, uterine cancer, chorionic cancer, thyroid cancer, malignant carcinoid tumor, skin cancer, malignant melanoma, osteosarcoma, soft-part tissue sarcoma, neuroblastoma, Wilms' tumor, retinoblastoma, melanoma, cancroid etc.

The pharmaceutical composition of the present invention may be used in combination with other pharmaceutical compositions.

If the bacteria of the genus *Bifidobacterium* having the gene coding for the converting enzyme introduced therein are administered, it is essential to administer a precursor of an antitumor substance. However, both the precursor of an antitumor substance and the bacteria of the genus *Bifidobacterium* having the gene coding for the converting enzyme introduced therein may constitute one pharmaceutical composition or may be administered separately at the same time or after a predetermined period.

Further, 20% lacturose is preferably used in combination. Lacturose is a nutrient source for the bacteria of the genus *Bifidobacterium* and cannot be metabolized by humans, mice and pigs so that by administering lacturose, the number of bacteria of the genus *Bifidobacterium* is increased specifically in tumor tissues.

The dose is preferably about 24 to 48 g/day for an adult, and the frequency of administration is not particularly limited.

Further, the pharmaceutical composition of the present invention can be used in combination with other antitumor agents. Generally, it is used preferably in combination with several kinds of antitumor agents which are different in the working mechanism.

The other antitumor agents include alkylating agents, various antimetabolites, antitumor antibiotics, other antitumor agents, antitumor plant components, BRM (biological response metabolite), angiogenesis inhibitors, cell adhesion inhibitors, matrix metalloprotease inhibitors, hormones, vitamins, antimicrobial antibiotics and chemotherapeutic agents.

Specifically, the alkylating agents include e.g. alkylating agents such as nitrogen mustard, nitrogen mustard N-oxide and chloram butyl; aziridine-type alkylating agents such as carboqoune and thio-TEPA; epoxide-type alkylating agents such as dibromomannitol and dibromodansitol; nitrosourea-type alkylating agents such as calmstine, romstine, semstine, nimustine hydrochloride, streptozotocin, chlorozotocin and ranimustine; busulfan; inprosulfane tocylate and dacarbazine.

The antimetabolites include e.g. purine antimetabolites such as 6-mercaptopurine, 6-thioguanine and thioinosine, pyrimidine antimetabolites such as fluorouracil, tegafur, tegafur uracil, carmofur, doxifluridine, broxuridine, cytarabine and enocitabine, folate antimetabolites such as methotrexate and trimethoxalate, as well as salts or complexes thereof.

The antitumor antibiotics include e.g. anthracycline-type antibiotic antitumor agents such as mitomycin C, bleomycin, peplomycin, daunorubicin, aclarubicin, doxorubicin, pyralbicin, THP-adriamycin, 4'-epidoxysorbicin and epirbicin, chromomycin $A_3$, actinomycin D etc. as well as salts or complexes thereof.

The other antitumor agents include e.g. cisplatin, carboplatin, tamoxifen, camptothecine, ifosfamide cyclophosphamide, melphalan, L-asparaginase, aceceratone, schizophyllan, picibanil, Ubenimex, crestine etc. as well as salts or complexes thereof. Further, procarbazine, pipobroman, neocarzinostatin, and hydroxyurea can also be mentioned.

The antitumor plant components include e.g. vinca alkaloids such as vindesine, vincristine and vinblastine, epipodophyllotoxines such as etoposide, teniposide etc., as well as salts or complexes thereof.

The BRM includes e.g. tumor necrosis factor, indomethacin and salts or complexes thereof.

The angiogenesis inhibitors include e.g. fumadirol derivatives and salts or complexes thereof.

The cell adhesion inhibitors include e.g. substances having the RGD sequence and salts or complexes thereof.

The matrix matalloprotease inhibitors include e.g. marimastat, batimastat and salts or complexes thereof.

The hormones include e.g. hydrocortisone, dexamethasone, methylprednisolone, prednisolone, plastelone, betamethasone, triamcinolone, oxymetholone, nandrolone, methenolone, fosfestorol, ethynylestradiol, chlormadinone, medroxyprogesterone etc. as well as salts or complexes thereof.

The vitamins include e.g. vitamin C, vitamin A and salts or complexes thereof.

The bacteria of the genus *Bifidobacterium* according to the present invention administered to the patient can be easily killed by antibiotics. This is important for further improvements in the safety of the gene delivery system of the present invention.

EXAMPLES

Hereinafter, the present invention is described by reference to the Examples, which however are not intended to limit the present invention. Unless otherwise specified, DNAs etc. in the Examples were handled according to the methods described in Molecular Cloning, Second Edition.

Example 1

Confirmation of Accumulation and Growth of *B. longum* in Tumor Tissues (1) Preparation of a Suspension of *B. longum* for Administration to Tumor-Bearing Animals A suspension of *B. longum* 105-A or 108A (Biosci. Biotech. Biochem., 61, 1211 (1997)) for administration to tumor-bearing animals was prepared in the manner described below. *B. longum* 105-A can be obtained by culturing FERM BP-7274 under non-selective conditions (in the absence of spectinomycin) in the manner described below, then plating it onto an agar-containing modified Briggs broth (modified Briggs broth containing 1.5% agar) to which 75 μg/ml spectinomycin had been added, and obtaining it as a strain rendered sensitive to spectinomycin by removal of a plasmid. *B. longum* 105-A or 108A was inoculated into a modified Briggs medium (a mixture of 100 parts of solution A, 10 parts of solution B and 1 part of solution C wherein the composition of each solution is as follows: solution A (0.5 g/l soluble starch, 6.0 g/l Bacto Yeast extract (Difco), 15.0 g/l polypeptone, 2.0 g/l sodium glutamate, 10.0 g/l sodium acetate.$3H_2O$, 4.0 g/l potassium dihydrogen phosphate, 5.0 g/l sodium chloride, 1.0 g/l Tween 80, 400 ml/l tomato juice extract (prepared by adding 400 ml water to 400 ml canned tomato juice (Delmonte), keeping it at 60° C. for 1 hour and then at 100° C. for 5 minutes, adding a small amount of High-Flow Super Cell (Wako Pure Chemical Industries, Ltd.) and filtering it by an aspirator), adjusted to pH 6.8 with sodium hydroxide and sterilized in an autoclave), solution B (20% aqueous lactose solution sterilized in an autoclave) and solution C (20.0 g/l L-cysteine, 340 g/l sodium ascorbate sterilized by filtration)). In this broth, the bacteria were multiplied by stationary culture under anaerobic conditions at 37° C. until their growth reached the middle phase of logarithmic growth phase.

The resulting culture liquid was centrifuged to precipitate the bacteria, and after the supernatant was removed, the bacteria were suspended in PBS (phosphate buffered saline, 8 g/l sodium chloride, 0.2 g/l potassium chloride, 1.44 g/l disodium hydrogen phosphate, 0.24 g/l potassium dihydrogen phosphate, pH 7.4), and the suspension was centrifuged further twice as described above, to wash the bacteria. After the second centrifugation, the supernatant was removed from the bacteria, which were then suspended in a 10- or 1/50-fold volume of PBS relative to the volume of the culture liquid subjected to the first centrifugation, whereby the *B. longum* suspension was prepared.

(2) Administration of *B. longum* into Tumor-Bearing Animals

The tumor-bearing animals for administration of *B. longum* were two kinds of tumor-bearing mice i.e. 6- to 8-week-old male C57BL/6 mice (purchased from Nippon SLC) transplanted with B16-F10 melanoma cells and Luwis lung cancer cells respectively, as well as tumor-bearing rats created by administering 7,12-dimethylbenz[a]anthracene (DMBA) to 6-week-old male Sparque-Dawley rats (purchased from Nippon SLC).

The B16-F10 melanoma cells and Luwis lung cancer cells used in inoculation into the mice were prepared by monolayer culture in a Dulbecco's modified Eagle's medium (Virology, 8, 396 (1959), Virology, 12, 185 (1960)) supplemented with 10% fetal bovine serum at 37° C. in an atmosphere of 5% $CO_2$. These cultured cancer cells, each $5 \times 10^5$ cells, were inoculated into the right thigh muscle of each C57BL/6 mouse, and in 2 weeks after this inoculation, the mice having the solid tumors in their right thighs were examined as the tumor-bearing mice in the *B. longum* injection test.

The rats with chemically induced breast cancer were created by administering 1 ml DABA (10 mg/ml) solution in sesame oil via a probe into the stomach of each 6-week-old male Sparque-Dawley rat, and one week later, an equal amount of DABA was administered again to the rat. In 1.5 to 2 months after the second administration, the rats having the tumor with a diameter of 5 mm were examined as the rats with chemically induced breast cancer in the *B. longum* injection test.

In administration of *B. longum* into the tumor-bearing animals, 0.5 ml (5 to $6 \times 10^6$ cells) suspension diluted 10-fold from the suspension of *B. longum* prepared in item (1) above were administered once via tail veins into the whole body of mouse, and 0.5 ml ($2 \times 10^8$ cells) suspension concentrated into a 1/50 volume from the suspension of *B. longum* prepared in item (1) above were administered once via tail veins into the whole body of rat, respectively.

(3) Observation of Selective Accumulation of *B. longum* in Tumor Tissues and Selective Growth Thereof in the Tumor Tissues Six to eight tumor-bearing mice to which *B. longum* had been administered were sacrificed at 1, 24, 48, 72, 96, and 168 hours respectively after injection, while 6 tumor-bearing rats were sacrificed at 168 hours after injection, and the tumor tissues and normal tissues were excised and each tissue extract was anaerobically cultured in order to analyze the accumulation and growth of *B. longum* in the tumor tissues and normal tissues.

The normal tissues used were obtained from the lung, liver, spleen, kidney and heart, and the mouse tumor tissues used were tumor tissues grown at the right tights, and the rat tumor tissues used were breast cancer tissues. After the tissues were weighed under aseptic conditions, the tissue extract was obtained by cutting the tissues, mashing, homogenizing them with ice-cold PBS in a 10-fold volume relative to the tissues and filtering.

Distribution of *B. longum* in each of the tissues was analyzed in the following manner. 100 µl sample (containing 0.01 g tissues/100 µl) prepared by diluting the tissue homogenate prepared above was put into two Petri dishes per sample, and a Briggs agar medium (prepared by adding 1.5% agar to the Briggs medium) at 55° C. containing 20 mg/l L-cysteine and 340 mg/l sodium ascorbate was poured into the Petri dish, and the medium was stirred well and then solidified by leaving it at room temperature. Each Petri dish was placed in a completely airtight desiccator at 37° C. under anaerobic conditions for 3 days, and the number of growing *B. longum* colonies therein was counted to analyze the distribution of *B. longum* in each tissue.

Figure 7:
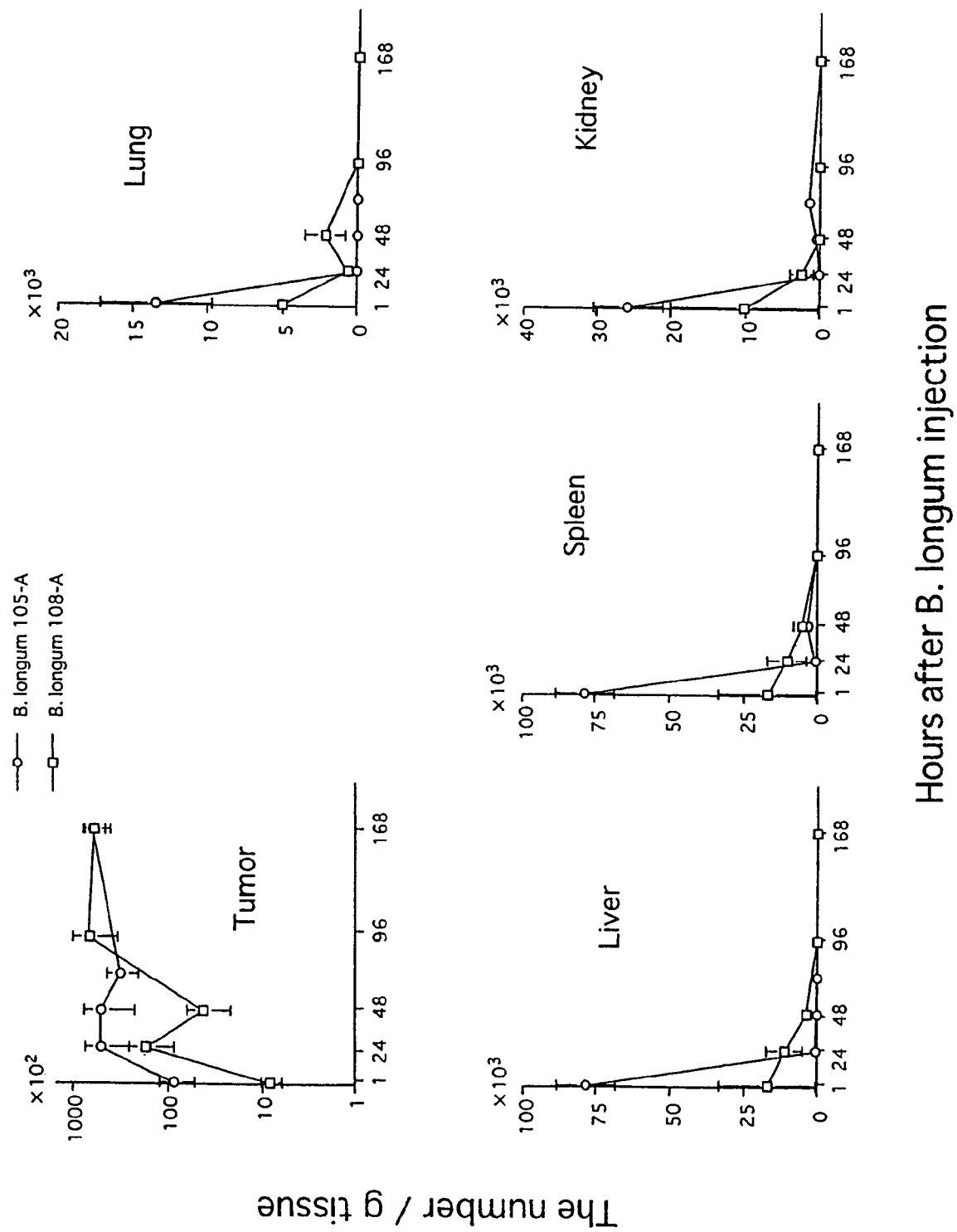
FIG. 7 is a graph showing the number of *B. longum* bacilli present in each kind of organ tissues and tumor tissues after intravenous injection of *B. longum* bacteria into tumor-bearing mice. The circle shows the result of administration of *B. longum* 105-A. The square shows the result of administration of *B. longum* 108-A.

As a result, 60,000 *B. longum* colonies per gram of the tumor tissues were observed in tumors of the tumor-bearing mice which underwent inoculation of the Lewis lung cancer cells and subsequent systemic administration of *B. longum* 105-A or 108-A respectively. On the other hand, no colony was observed in the normal tissues, that is, the lung, liver, spleen, kidney and heart after 96 hours with *B. longum* 108-A and after 168 hours with *B. longum* 105-A (FIG. 7).

The same results as above were obtained in the case of the tumor-bearing mice, which underwent inoculation with B16-F10 melanoma cells and subsequent administration of *B. longum* 105-A or 108-A.

Figure 8:
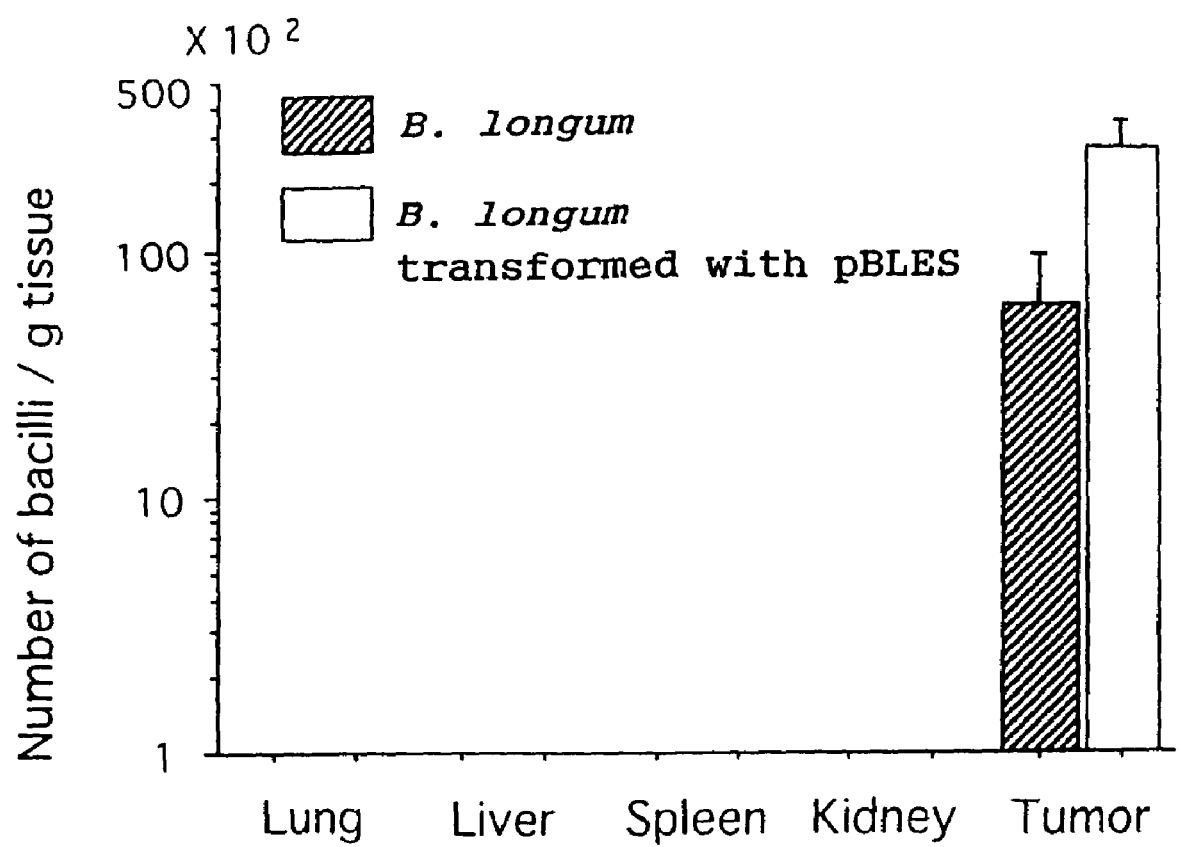
FIG. 8 is a graph showing the number of *B. longum* bacilli present in each kind of organ tissues and tumor tissues in 168 hours after intravenous injection of *B. longum* 105-A (shown in the netted bar) or *B. longum* 105-A transformed with pBLES100 (shown in the white bar) into tumor-bearing rats.

10,000 *B. longum* colonies per gram of the tumor tissues were observed in tumors of the rats with chemically induced breast cancer, which underwent systemic administration of *B. longum* 105-A, but no colony was observed in the normal tissues, that is, the lung, liver, spleen and kidney after 168 hours (FIG. 8).

From the results described above, it was confirmed that *B. longum* was accumulated and multiplied in tumor tissues specifically.

(4) Growth of *B. longum* in Tumor Tissues by Administering Lacturose (4-0-β-D-galactopyranosyl-D-fructofuranose)

Lacturose (provided by Nikken Chemicals Co., Ltd.) is a synthetic saccharide not occurring in nature, and it is known that lacturose cannot be metabolized by humans, mice and pigs (Biochem. Biophys. Acta, 110, 635 (1965), Pediatrics, 32, 1033 (1963), Gastroenterology, 47, 26 (1964), Die Nahrung, 11, 39 (1967)). On the other hand, *B. longum* is capable of growing with lacturose as a carbon source.

Accordingly, 6 to 8 mice bearing Lewis lung cancer cells to which *B. longum* 105-A had been administered was intraperitoneally given 1 ml of 20 t lacturose solution for 8 successive days after injection of *B. longum*, and on the 9th day, the mice were sacrificed to analyze the number of *B. longum* bacteria present in each tissue. As a result, the number of *B. longum* bacteria present of the tumor tissues in the tumor-bearing mouse group given lacturose was 200-times as more as that of the control group not given lacturose.

From the results described above, it was demonstrated that *B. longum* in tumor tissues can be selectively grown by administration of lacturose.

Example 2

Specific Accumulation and Growth of Recombinant *B. longum* Having Plasmid DNA in Tumor Tissues (1) Preparation of Recombinant *B. longum* Having Plasmid DNA According to the method described in Example 1 (1), *B. longum* 105-A was cultured under anaerobic conditions and then left at 4° C. Then, the culture liquid was centrifuged to precipitate the bacteria, and after the supernatant was removed, the bacteria were suspended in ice-cold 10% glycerol. The operation described above was repeated 3 times, whereby the *B. longum* bacteria were sufficiently washed. After the final washing, the supernatant was removed, and the bacteria were suspended in ice-cold 10% glycerol in a 1/10 volume relative to the volume of the culture liquid subjected to the first centrifugation and used as a bacterial sample to be subjected to transformation by electroporation ($2 \times 10^8$ to $2 \times 10^9$ colony forming unit (CFU)/50 µl).

The plasmid DNA used in transformation, that is, plasmid pBLES100 (Biosci. Biotech. Biochem., 61, 1211 (1977)) can be constructed by the method described in Biosci. Biotech. Biochem., 61, 1211 (1997) or can be obtained by extracting the plasmid in a usual manner from FERM BP-7274 deposited with the National Institute of Bioscience and Human-Technology, Agency of Industrial Science and Technology, then digesting the DNA with restriction enzyme Hind III (Takara Shuzo Co., Ltd.), treating the DNA with phenol, precipitating it with ethanol and dissolving it in e.g. water, followed by ligation thereof through self-cyclization reaction with T4 DNA ligase (Takara Shuzo Co., Ltd.) according to manufacture's instructions.

Plasmid pBLES100 used for transformation of *B. longum* was prepared in the following manner. Plasmid pBLES100 obtained in the manner as described above was used to transform *E. coli* JM109, and the resulting transformant was cultured in the presence of 75µ/ml spectinomycin. Plasmid pBLES100 was extracted in a usual manner from the culture obtained in this culture and purified by cesium chloride density gradient ultracentrifugation (Molecular Cloning, Second Edition), to give plasmid pBLES100 for use in transformation of *B. longum*.

50 µl of the *B. longum* 105-A sample and 4 µl of plasmid pBLES100 (1 µg DNA/4 µl) prepared above were put to an electroporation cuvette of 0.2 cm in width (Bio-Rad), mixed and placed on ice for 5 minutes. The cuvette was set in Gene Pulser (Bio-Rad) and subjected to transformation by electroporation under the conditions of 2.0 KV, 25 µF capacitor and 200Ω parallel resistance.

After electric pulses were applied, 1 ml Briggs medium was rapidly added to the cuvette, and after the cuvette was left at 37° C. for 3 hours, the sample in the cuvette was plated onto a Briggs agar medium plate containing 75 µg/ml spectinomycin. The plate was incubated at 37° C. for 3 to 4 days under anaerobic conditions in Gas Pack Anaerobic Systems (BBL).

A few of the resulting colonies were picked up and cultured in the method described in Example 1 (1), and the plasmid DNA possessed by the colonies was extracted by using QIAGEN Plasmid Mini Kit (Qiagen) according to manufacture's instruction provided that lysozyme was added to a P1 solution obtained by lyzing the bacteria and then the solution was incubated at 37° C. for 40 minutes.

The plasmid DNA thus extracted was digested with several restriction enzymes and its structure was confirmed by agarose gel electrophoresis, and it was confirmed that the colonies carried pBLES100.

The resulting recombinant was designated *B. longum* 105-A/pBLES100.

(2) Administration of Recombinant *B. longum* into Tumor-Bearing Animals

A suspension of *B. longum* 105-A/pBLES100 for use in administration into tumor-bearing animals was prepared in the same manner as in Example 1 (1) except that 75 µg/ml spectinomycin was added to the modified Briggs medium.

The suspension was administered in the same manner as in Example 1 (2) into tumor-bearing mice transplanted with B16-F10 melanoma cells and into tumor-bearing rats with chemically induced breast cancer.

(3) Selective Accumulation and Growth of the Recombinant *B. longum* in Tumor Tissues Six to eight tumor-bearing mice and 6 tumor-bearing rats to which the suspension of *B. longum* 105-A/pBLES100 had been administered were sacrificed on the fourth day, and the distribution of *B. longum* 105-A/pBLES100 in the tumor tissues and normal tissues was analyzed according to the method described in Example 1 (3). However, 75 µg/ml spectinomycin was added to the medium mixed with the tissue extract.

Figure 9:
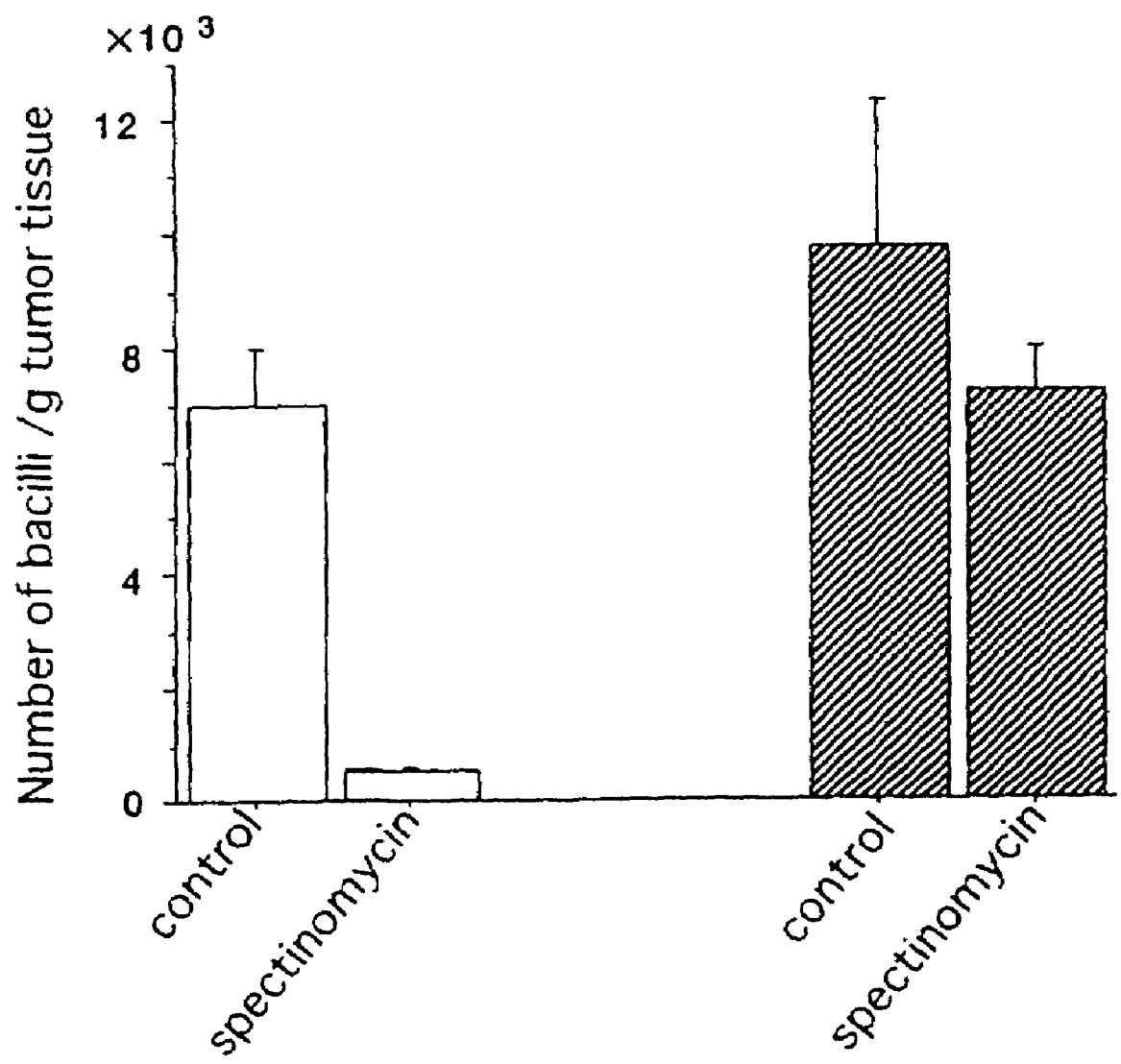
FIG. 9 is a graph showing the number of *B. longum* bacilli present tumor cells after intravenous injection of *B. longum* 105-A or *B. longum* 105-A/pBLES100 and administration of spectinomycin into tumor-bearing mice. The white bar indicates a group given *B. longum* 105-A, and the netted bar indicates a group given *B. longum* 105-A/pBLES100, and the control shows a group not given spectinomycin, and spectinomycin shows a group given spectinomycin.

As a result, the tumor-bearing mice inoculated with B16-F10 melanoma cells or Luwis lung cancer cells did not indicate a reduction in the number of cells of *B. longum* 105-A/pBLES100 distributed in the tumor tissues in the tumor-bearing mice given *B. longum* 105-A/pBLES100, as compared with the number of cells of *B. longum* distributed in the tumor tissues in the control group given non-recombinant *B. longum* 105-A (FIG. 9). Further, the rats with chemically induced breast cancer gave the same results (FIG. 8).

From the results described above, it was found that in tumor tissues, *B. longum* 105-A can stably maintain plasmid pBLES100.

Those tumor-bearing mice into which non-recombinant *B. longum* or *B. longum* 105-A/pBLES100 had been administered were intraperitoneally given 200 mg/kg spectinomycin every day from the next day of administration, and the mice were sacrificed on the fourth day, and distribution of *B. longum* in each tissue was analyzed.

The number of bacteria of *B. longum* distributed in the tumor tissues was reduced to 1% or less by giving spectinomycin to the tumor-bearing mice into which non-recombinant *B. longum* had been administered, as compared with the control group given daily intraperitoneally PBS in place of spectinomycin. In the tumor-bearing mice into which *B. longum* 105-A/pBLES100 had been administered, the number of bacteria of *B. longum* 105-A/pBLES100 distributed in the tumor tissues was kept at 81% of the number of bacteria in the control group (FIG. 9).

From the results described above, it was confirmed that the spectinomycin resistance gene is expressed specifically in the tumor tissues.

Example 3

Antitumor Agent Containing Recombinant *B. longum* Highly Expressing Cytosine Deaminase (CD) Gene (1) Acquisition of the Gene Highly Expressed in *B. longum* Cells The HU gene (HU protein: histone-like DNA-binding protein, Biochimie, 72, 207 (1990)) known as a gene highly expressed in *B. longum* cells was obtained in the following manner.

*B. longum* ATCC15707 was cultured in the Briggs medium according to the method described in Example 1 (1), and from the resulting bacterium, chromosomal DNA was extracted and purified according to the method described in Molecular Cloning, Second Edition. 1 µg of the chromosomal DNA was digested with restriction enzyme HindIII and purified by treatment with phenol and precipitation with ethanol. Separately, plasmid pBR322 (purchased from Takara Shuzo Co., Ltd.) was also digested with Hind III, dephosphorylated and purified in analogous manner. 100 ng each of the DNAs were ligated by use of T4 DNA ligase (Takara Shuzo Co., Ltd.) according to manufacture's instructions, to give recombinant DNA.

Then, the recombinant DNA was used to transform *E. coli* mH3 (Gene, 45, 37 (1986)), to give transformants resistant to ampicillin and sensitive to tetracycline.

From about 2000 transformants thus obtained, plasmid DNA was extracted therefrom in a usual manner and transformed into *E. coli* YK2741 (Gene, 89, 133 (1990)). The YK2741 strain is a strain deficient in the HU gene and an IHF (integration host factor) gene and thus sensitive to low temperatures. Accordingly, a transformant capable of growing even at low temperatures can be a strain carrying the HU gene derived from *B. longum*. Transformation was carried out in a usual manner, and the transformants were plated onto an ampicillin-containing agar medium and cultured at 27° C., and the growing transformants were subjected to the subsequent experiment.

Then, the transformants of YK2741 strain obtained above were cultured, and the plasmid possessed by each transformant was extracted by the method described above and transformed into *E. coli* YK1340 (J. Mol. Biol., 204, 581 (1988)). The resulting transformants were examined in a Mu phage transfection test according to the method described in Molecular Cloning, Second Edition. The YK1340 strain is a strain deficient in the HU gene, but Mu phage necessitates the HU protein for its growth, and thus its transformant infected with Mu phage and lyzed by growth of Mu phage is a promising candidate for a strain carrying the HU gene derived from *B. longum*.

Figure 10:
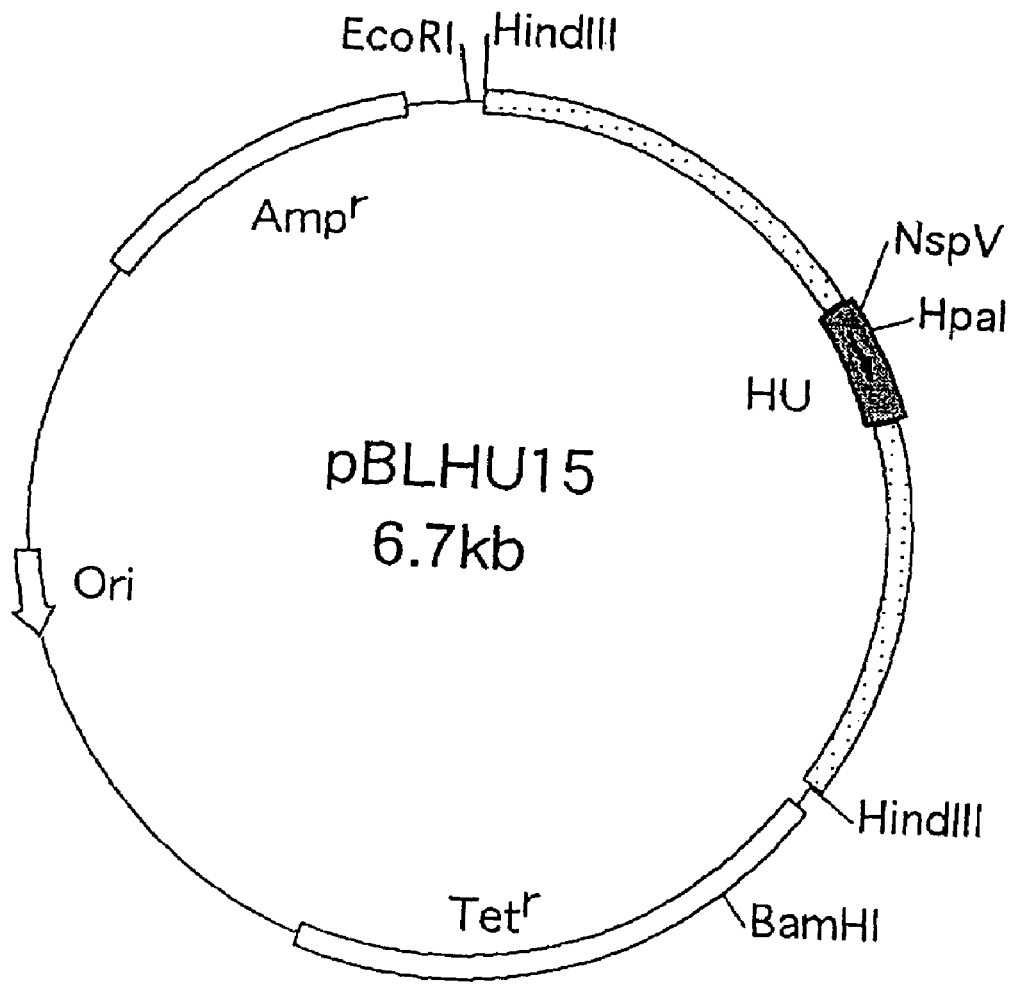
FIG. 10 shows an illustration of plasmid pBLHU15 containing DNA coding for HU protein derived from *B. longum*. The dotted part is a Hind III-treated fragment of the gene from *B. longum*, the solid line and the non-smeared part indicate plasmid pBR322, and the smeared part is the HU gene derived from *B. longum*. $Amp^r$ represents an ampicillin resistance gene, $Ter^r$ represents a tetracycline resistance gene and Ori represents an origin of replication.

One of the plasmids possessed by the transformants resistant to ampicillin and infected with Mu phage and lyzed by growth of Mu phage was designated pBLHU15, and its structure and properties were analyzed, and said plasmid was confirmed to be a plasmid carrying the HU gene derived from *B. longum* (FIG. 10).

(2) Preparation of a Plasmid Highly Expressing Cytosine Deaminase (CD) Gene

A gene coding for CD was obtained by PCR where plasmid pAdex1CSCD (RDB No. 1591, Gene Bank, Institute of Physical and Chemical Research) containing a gene coding for CD derived from *E. coli* was used as the template, while the DNA set forth in SEQ ID NO: 2 and the DNA in SEQ ID NO: 3 were used as a primer set. In PCR, 40 µl reaction solution (125 ng/l template DNA, 0.5 µmol/l each primer, 2.5 units Pfu DNA polymerase (Stratagene), 4 µl of ×10 buffer for Pfu DNA polymerase (Stratagene) and 200 µmol/l each deoxy NTP) was subjected repeatedly 30 times to the step of reaction at 94° C. for 1 min., 55° C. for 1 min. and 72° C. for 1 min., and then the reaction solution was kept at 72° C. for 15 minutes.

After it was confirmed by agarose gel electrophoresis of an aliquot of the reaction solution that an about 1.3-kb fragment had been amplified, the remainder of the reaction solution was purified by treatment with phenol and precipitation with ethanol, and the fragment was ligated to TOPO vector (Funakoshi) by use of T4 DNA ligase. The recombinant DNA thus obtained by ligation was used to transform E. coli JM109, then the plasmid DNA was extracted from the resulting transformant, and digested with various restriction enzyme, it was confirmed that the desired plasmid pTOPO-eCD had been constructed carrying out agarose gel electrophoresis of the digests. Plasmid pTOPO-eCD was digested with restriction enzymes Nsp V (Takara Shuzo Co., Ltd.) and Hpa I (Takara Shuzo Co., Ltd.) and then electrophoresed on agarose gel, and the about 1.3-kb DNA fragment coding for CD was purified by Gene clean kit (Funakoshi) according to manufacturer's instructions.

Separately, plasmid pBLHU15 obtained in Example 3 (1) was also digested with Nsp V and Hpa I and a 6.7-kb DNA fragment was purified.

The 1.3-kb DNA fragment and the 6.7-kb DNA fragment obtained above were ligated by use of T4 DNA ligase to prepare a recombinant DNA, and this recombinant DNA was used to transform E. coli JM109 in a usual manner. Some of the resulting transformants were cultured, and the plasmid was extracted from the culture, then digested with various restriction enzymes and analyzed by agarose gel electrophoresis, and it was thus confirmed that the plasmid DNA having the CD gene integrated downstream from the promoter for the HU gene had been constructed.

The plasmid DNA was then digested with Hind III and electrophoresed on agarose gel to separate a 3.6-kb DNA fragment containing the HU gene and the CD-coding gene, followed by purification thereof by the Gene Clean kit. Further, the *Escherichia-Bifidobacterium* shuttle vector pBLES100 described above was also digested with Hind III and dephosphorylated.

The 3.6-kb DNA fragment and the Hind III digest of pBLES100 obtained above were ligated by use of T4 DNA ligase to construct a recombinant DNA, and this recombinant DNA was used to transform E. coli JM109 in a usual manner.

A few of the transformants having spectinomycin resistance were picked up, and the plasmid DNA possessed by the transformants was extracted in a usual manner, then digested with various restriction enzymes and subjected to agarose gel electrophoresis, and it was thereby confirmed that the desired plasmid had been constructed.

Figure 11:
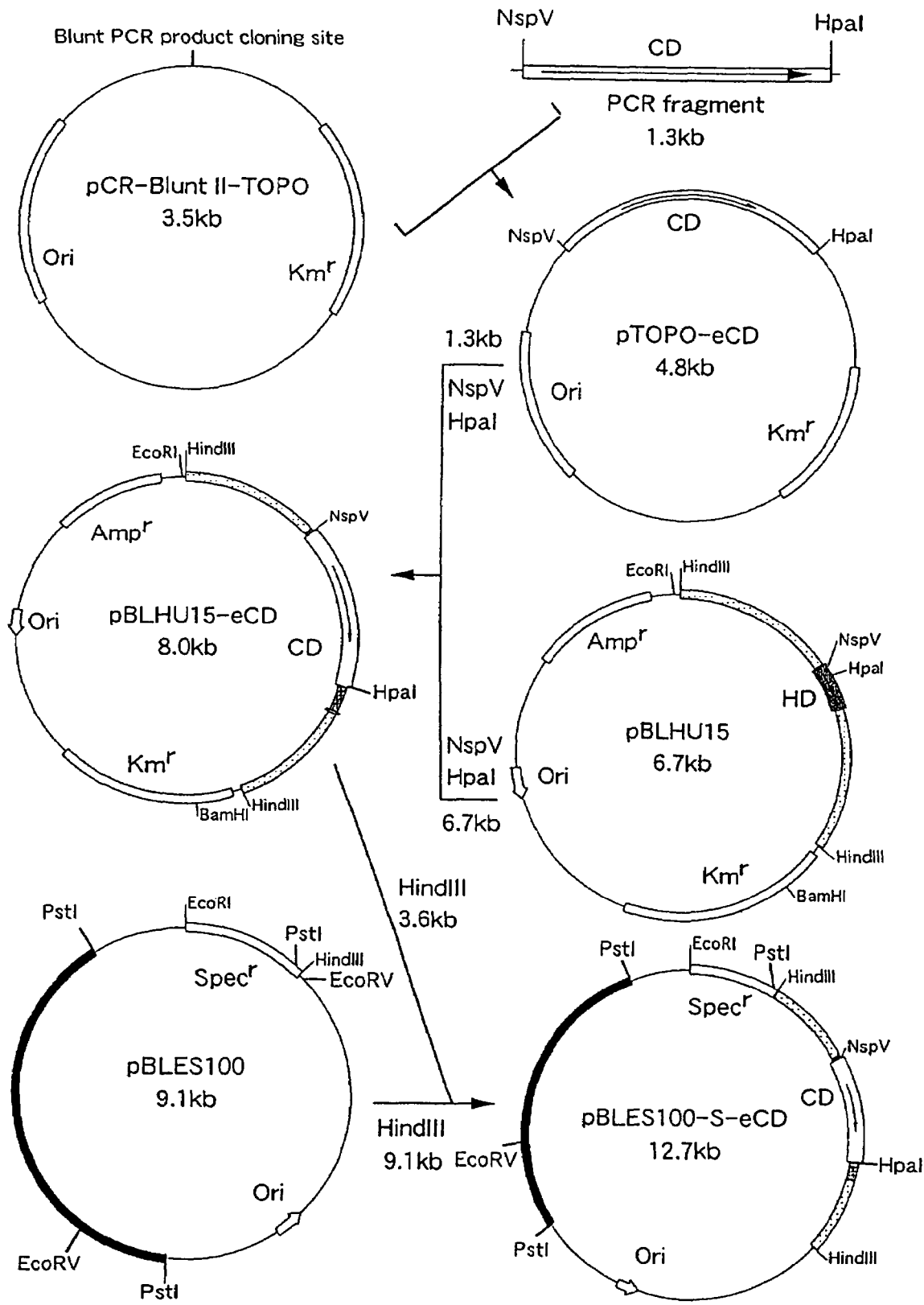
FIG. 11 shows a process for constructing plasmid vector pBLES100-S-eCD in which the CD gene derived from *Escherichia coli* was integrated, which is used as expression vector for *B. longum*.

The resulting *Escherichia-Bifidobacterium* shuttle vector having the CD-coding gene downstream from the promoter for the HU gene was designated pBLES100-S-eCD (FIG. 11).

From E. coli JM109 carrying the plasmid pBLES100-S-eCD obtained above, the plasmid for use in transformation of B. longum was prepared by cesium chloride density gradient centrifugation according to the method described in Example 2 (1). The plasmid pBLES100-S-eCD thus prepared was used to transform B. longum 105-A in the method described in Example 2 (1), and the resulting transformant strain was designated B. longum 105-A/pBLES100-S-eCD.

The transformant B. longum 105-A/pBLES100-S-eCD has been deposited under FERM BP-7274 under the Budapest Treaty with the National Institute of Bioscience and Human-Technology, Agency of Industrial Science and Technology, the Ministry of International Trade and Industry, Higashi 1-1-3, Tsukuba City, Ibaraki Pref. Japan (Zip Code: 305-8566) from Aug. 15, 2000.

Example 4

Antitumor Agent Containing Recombinant B. longum Highly Expressing CD Gene (1) Injection of B. longum 105-A/pBLES100-S-eCD into Tumor-Bearing Animals A suspension of B. longum 105-A/pBLES100-S-eCD used for injection to tumor-bearing mice was prepared according to the method described in Example 2 (2).

The suspension containing $1 \times 10^7$ bacteria was injected topically into tumors in the thigh of each tumor-bearing mouse transplanted with B16-F10 melanoma cells in the right thigh.

(2) Specific Conversion of 5-fluorocytosine (5-FC) into 5-fluorouracil (5-FU) in Tumor Tissues 500 mg/kg 5-FC was administered intraperitoneally every day into 6 to 8 tumor-bearing mice to which B. longum 105-A/pBLES100-S-eCD had been injected in Example 4 (1), while 1 ml of 20% lacturose solution was administered intraperitoneally every day into each mice from the next day of administration of B. longum 105-A/pBLES100-S-eCD. The administration was conducted until the tumor-bearing mice were sacrificed. Separately, 5-FC was administered every day in the same manner as above into the control group of tumor-bearing mice to which B. longum 105-A/pBLES100-S-eCD was not administered.

On the 8th day after injection of B. longum 105-A/pBLES100-S-eCD, the tumor-bearing mice were sacrificed, and the concentration of 5-FU in the tumor tissues in the thighs was examined. For measurement of the concentration of 5-FU, the tumor tissues to which the transformant B. longum 105-A/pBLES100-S-eCD had been topically injected, and the tumor tissues to which the transformant had not been injected were excised, and the concentration of 5-FU in the tumor tissues was measured by GC-MS method (J. Chromatography, 564, 137 (1991)) in Otsuka Assay Laboratories.

As a result, only about 10.0 ng/g 5-FU could be detected in the tumor tissues to which B. longum 105-A/pBLES100-S-eCD had not injected, while 588.8 ng/g 5-FU was detected in the tumor tissues to which B. longum 105-A/pBLES100-S-eCD had been topically injected.

From the results described above, it was confirmed that systemically administered 5-FC is converted into 5-FU in tumor tissues specifically.

INDUSTRIAL APPLICABILITY

The present invention provides a method of expressing a substance having an antitumor activity or a converting enzyme in tumor tissues specifically under anaerobic conditions by using, as gene delivery vectors, anaerobic bacteria belonging to the genus *Bifidobacterium*, some of which are domestic in human intestine and nonpathogenic bacteria, as well as transformed or mutated bacteria belonging to the genus *Bifidobacterium* for use in said method.

By use of this method in treating solid tumors, there is the effect that selective treatment of tumors is feasible and the side effect of a conventional chemotherapeutic agent against tumors is relieved. Also, there is another effect that those compositions which were effective against cancer but could not be used due to their side effects may become usable.

Further, the present invention provides an expression vector for high expression of a protein encoded by DNA introduced into bacteria of the genus *Bifidobacterium*. Tumor tissues particularly solid tumors under anaerobic conditions can thereby be efficiently treated.

What is claimed is:

1. A nonpathogenic bacterium of the genus *Bifidobacterium*, comprising a vector that comprises:
   a) a Bifidobacterium histone-like DNA binding protein (HU protein) promoter, a DNA sequence downstream of the promoter that encodes i) a protein with anti-tumor activity or ii) a protein that converts a precursor of an antitumor substance into an antitumor substance, and a HU protein terminator downstream of the DNA sequence; and
   b) a selective marker selected from the group consisting of antibiotic resistance markers, nutritional requirement markers, and medium selection markers.

2. The bacterium of claim 1, wherein the vector autonomously replicates in the bacterium.

3. The bacterium of claim 1, wherein the vector is integrated in the genomic DNA of the bacterium.

4. The bacterium of claim 1, wherein the vector is an *E. coli-Bifidobacterium* shuttle vector.

5. The bacterium of claim 1, wherein the HU protein promoter and terminator are a *Bifidobacterium longum* promoter and terminator.

6. The bacterium of claim 5, wherein the HU protein promoter has the DNA sequence of nucleotides 1-192 of SEQ ID NO:1.

7. The bacterium of claim 5, wherein the HU protein terminator has the DNA sequence of nucleotides 472-600 of SEQ ID NO:1.

8. The bacterium of claim 6, wherein the HU protein terminator has the DNA sequence of nucleotides 472-600 of SEQ ID NO:1.

9. The bacterium of claim 1, wherein the vector is pBLES100-S-eCD.

10. The bacterium of claim 1, wherein the bacterium is *Bifidobacterium longum* 105/pBLES100-S-eCD (accession no FERM BP-7274).

11. The bacterium of claim 1, wherein the bacterium is a *Bifidobacterium adolescentis, Bifidobacterium longum, Bifidobacterium bifidum, Bifidobacterium breve*, or a *Bifidobacterium infantis* bacterium.

12. The bacterium of claim 11, wherein the bacterium is a *Bifidobacterium longum* bacterium.

13. The bacterium of claim 1, wherein the DNA sequence encodes a protein that converts a precursor of an antitumor substance into an antitumor substance.

14. The bacterium of claim 13, wherein the protein is cytosine deaminase, nitroreductase, herpes simplex virus type 1 protein thymidine kinase, or β-glucuronidase.

15. The bacterium of claim 14, wherein the protein is a cytosine deaminase.

16. The bacterium of claim 1, wherein the bacterium is a *Bifidobacterium longum* bacterium and wherein the protein that converts a precursor of an antitumor substance into an antitumor substance is a cytosine deaminase.

17. A composition comprising the bacterium of claim 1 and an aqueous medium suitable for administration to a human.

18. The bacterium of claim 6, wherein the bacterium is a *Bifidobacterium adolescentis, Bifidobacterium longum, Bifidobacterium bifidum, Bifidobacterium breve*, or a *Bifidobacterium infantis* bacterium.

19. The bacterium of claim 18, wherein the bacterium is a *Bifidobacterium longum* bacterium.

20. The bacterium of claim 6, wherein the DNA sequence encodes a protein that converts a precursor of an antitumor substance into an antitumor substance.

21. The bacterium of claim 20, wherein the protein is cytosine deaminase, nitroreductase, herpes simplex virus type 1 protein thymidine kinase, or β-glucuronidase.

22. The bacterium of claim 21, wherein the protein is a cytosine deaminase.

23. The bacterium of claim 6, wherein the bacterium is a *Bifidobacterium longum* bacterium and wherein the protein that converts a precursor of an antitumor substance into an antitumor substance is a cytosine deaminase.

24. A composition comprising the bacterium of claim 6 and an aqueous medium suitable for administration to a human.

* * * * *

SEQUENCE LISTING

<160> NUMBER OF SEQ ID NOS: 4

<210> SEQ ID NO 1
<211> LENGTH: 600
<212> TYPE: DNA
<213> ORGANISM: Bifidobacterium longum
<220> FEATURE:
<221> NAME/KEY: CDS
<222> LOCATION: (193)..(471)

<400> SEQUENCE: 1

```
gctgggcgcg gcggccatga agtggcttga caagcataat cttgtctgat tcgtctattt      60
tcaataccct cggggaaata gatgtgaaaa cccttataaa acgcgggttt tcgcagaaac     120
atgcgctagt atcattgatg acaacatgga ctaagcaaaa gtgcttgtcc cctgacccaa     180
gaaggatgct tt atg gca tac aac aag tct gac ctc gtt tcg aag atc gcc     231
              Met Ala Tyr Asn Lys Ser Asp Leu Val Ser Lys Ile Ala
                1               5                  10 cag aag tcc aac ctg acc aag gct cag gcc gag gct gct gtt aac gcc       279
Gln Lys Ser Asn Leu Thr Lys Ala Gln Ala Glu Ala Ala Val Asn Ala
     15                  20                  25 ttc cag gat gtg ttc gtc gag gct atg aag tcc ggc gaa ggc ctg aag       327
Phe Gln Asp Val Phe Val Glu Ala Met Lys Ser Gly Glu Gly Leu Lys
 30                  35                  40                  45 ctc acc ggc ctg ttc tcc gct gag cgc gtc aag cgc ccg gct cgc acc       375
Leu Thr Gly Leu Phe Ser Ala Glu Arg Val Lys Arg Pro Ala Arg Thr
                 50                  55                  60 ggc cgc aac ccg cgc act ggc gag cag att gac att ccg gct tcc tac       423
Gly Arg Asn Pro Arg Thr Gly Glu Gln Ile Asp Ile Pro Ala Ser Tyr
             65                  70                  75 ggc gtt cgt atc tcc gct ggc tcc ctg ctg aag aag gcc gtc acc gag       471
Gly Val Arg Ile Ser Ala Gly Ser Leu Leu Lys Lys Ala Val Thr Glu
         80                  85                  90 tgaccttctg ctcgtagcga ttacttcgag cattactgac gacaaagacc ccgaccgaga     531
tggtcggggt cttttttgttg tggtgctgtg acgtgttgtc caaccgtatt attccggact     591
agttcagcg                                                             600
```

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ggttcgaata acgcttta                                                    18

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
cggttaactc aacgtttgta atc                                              23

<210> SEQ ID NO 4

-continued

```
<211> LENGTH: 93
<212> TYPE: PRT
<213> ORGANISM: Bifidobacterium longum

<400> SEQUENCE: 4

Met Ala Tyr Asn Lys Ser Asp Leu Val Ser Lys Ile Ala Gln Lys Ser
 1               5                  10                  15

Asn Leu Thr Lys Ala Gln Ala Glu Ala Ala Val Asn Ala Phe Gln Asp
            20                  25                  30

Val Phe Val Glu Ala Met Lys Ser Gly Glu Gly Leu Lys Leu Thr Gly
        35                  40                  45

Leu Phe Ser Ala Glu Arg Val Lys Arg Pro Ala Arg Thr Gly Arg Asn
    50                  55                  60

Pro Arg Thr Gly Glu Gln Ile Asp Ile Pro Ala Ser Tyr Gly Val Arg
65                  70                  75                  80

Ile Ser Ala Gly Ser Leu Leu Lys Lys Ala Val Thr Glu
                85                  90
```